(12) United States Patent
Chou et al.

(10) Patent No.: US 11,118,201 B2
(45) Date of Patent: Sep. 14, 2021

(54) HETEROLOGOUS EXPRESSION OF CARBOHYDRATE BINDING MODULES AND USES THEREOF FOR CADAVERINE PRODUCTION

(71) Applicants: CATHAY BIOTECH INC., Shanghai (CN); CIBT America Inc., Newark, DE (US)

(72) Inventors: Howard Chou, Shanghai (CN); Ling Chen, Shanghai (CN); Xiucai Liu, Shanghai (CN)

(73) Assignees: CATHAY BIOTECH INC., Shanghai (CN); CIBT America Inc., Newark, DE (US)

( * ) Notice: Subject to any disclaimer, the term of this patent is extended or adjusted under 35 U.S.C. 154(b) by 0 days.

(21) Appl. No.: 16/648,194

(22) PCT Filed: Sep. 22, 2017

(86) PCT No.: PCT/CN2017/102884
§ 371 (c)(1),
(2) Date: Mar. 17, 2020

(87) PCT Pub. No.: WO2019/056285
PCT Pub. Date: Mar. 28, 2019

(65) Prior Publication Data
US 2020/0255873 A1  Aug. 13, 2020

(51) Int. Cl.
| | |
|---|---|
| *C12P 13/00* | (2006.01) |
| *C12N 1/21* | (2006.01) |
| *C12N 9/88* | (2006.01) |
| *C07K 19/00* | (2006.01) |
| *C07K 14/245* | (2006.01) |
| *C12N 1/20* | (2006.01) |

(52) U.S. Cl.
CPC .......... *C12P 13/001* (2013.01); *C07K 14/245* (2013.01); *C12N 1/20* (2013.01); *C12N 9/88* (2013.01); *C12Y 401/01018* (2013.01); *C07K 2319/035* (2013.01); *C07K 2319/20* (2013.01); *C12N 2510/02* (2013.01)

(58) Field of Classification Search
None
See application file for complete search history.

(56) References Cited

U.S. PATENT DOCUMENTS

| | | |
|---|---|---|
| 2013/0095534 A1 | 4/2013 | Mimitsuka et al. |
| 2014/0356916 A1 | 12/2014 | Wittmann et al. |
| 2017/0044581 A1 * | 2/2017 | Lee ................... C12N 15/70 |
| 2017/0226544 A1 | 8/2017 | Wen et al. |

FOREIGN PATENT DOCUMENTS

| | | | |
|---|---|---|---|
| CN | 105316270 A | 2/2016 | |
| WO | WO-2017079872 A1 * | 5/2017 | ........... C07K 14/245 |

OTHER PUBLICATIONS

Ikeda et al., Direct cadaverine production from cellobiose using beta-glucosidase displaying *Escherichia coli*, AMB Express 3, 2013, 67.*
Kim et al., Bi-functional cellulases complexes displayed on the cell surface of Corynebacterium glutamicum increase hydrolysis of lignocelluloses at elevated temperature, Enzyme Microbial Technol. 66, 2014, 67-73.*
Lee et al., Microbial cell-surface display, Trends Biotechnol. 21, 2003, 45-52. (Year: 2003).*
Francisco et al., Specific adhesion and hydrolysis of cellulose by intact *Escherichia coli* expressing surface anchored cellulase or cellulose binding domains, Bio/Technology 11, 1993, 491-95. (Year: 1993).*
Bhatia et al., Biotransformation of lysine into cadaverine using barium alginate-immobilized *Escherichia coli* overexpressing CadA, Bioprocess. Biosyst. Eng. 28, 2015, 2315-22. (Year: 2015).*
Uniprot, Accession No. P0A910, 2017, www.uniprot.org. (Year: 2017).*
Georgiou et al., Display of beta-lactamase on the *Escherichia coli* surface, Protein Eng. 9, 1996, 239-247. (Year: 1996).*
International Search Report for Application No. PCT/CN2017/102884, dated Mar. 30, 2018.
Dongxia Li et al., "Progress in biosythesis of diaminopentane", *Chinese Journal of Biotechnology*, vol. 30, No. 2, pp. 161-174 (2014).
Weichao Ma et al., "Enhanced cadaverine production from L-lysine using recombinant *Escherichia coli* co-overexpressing CadA and CadB", *Biotechnology Letters*, vol. 37, pp. 799-806 (2015).
Kenta Imao et al., "1,5-Diaminopentane production from xylooligosaccharides using metabolically engineered *Corynebacterium glutamicum* displaying beta-xylosidase on the cell surface", *Bioresource Technology*, vol. 245, pp. 1684-1691 (2017).
Tsutomu Tanaka et al., "Creation of a Cellooligosaccharide Assimilating *Escherichia coli* Strain by Displaying Active Beta-Glucosidase on the Cell Surface via a Novel Anchor Protein", *Applied and Environmental Microbiology*, vol. 77, No. 17, pp. 6265-6270 (2011).
Shashi Kant Bhatia et al., "Biotransformation of lysine into cadaverine using barium alginate-immobilized *Escherichia coli* overexpressing CadA", *Bioprocess and Biosystems Engineering*, vol. 38, No. 12, pp. 2315-2322 (2015).

(Continued)

*Primary Examiner* — Tekchand Saidha
*Assistant Examiner* — Todd M Epstein
(74) *Attorney, Agent, or Firm* — Marshall, Gerstein & Borun LLP

(57) ABSTRACT

The invention provides microorganisms genetically modified to co-overexpress a carbohydrate binding module and lysine decarboxylase polypeptides in a mesophilic host to enhance the production of lysine derivatives by the microorganism, method of generating such microorganism, and methods of producing lysine derivatives using the genetically modified microorganisms.

12 Claims, 1 Drawing Sheet
Specification includes a Sequence Listing.

(56) References Cited

OTHER PUBLICATIONS

Aijun A. Wang et al., "Whole-Cell Immobilization Using Cell Surface-Exposed Cellulose-Binding Domain", *Biotechnology Progress*, vol. 17, No. 3, pp. 407-411 (2001).
Extended European Search Report for Application No. EP 17925645.8, dated May 11, 2021.

* cited by examiner

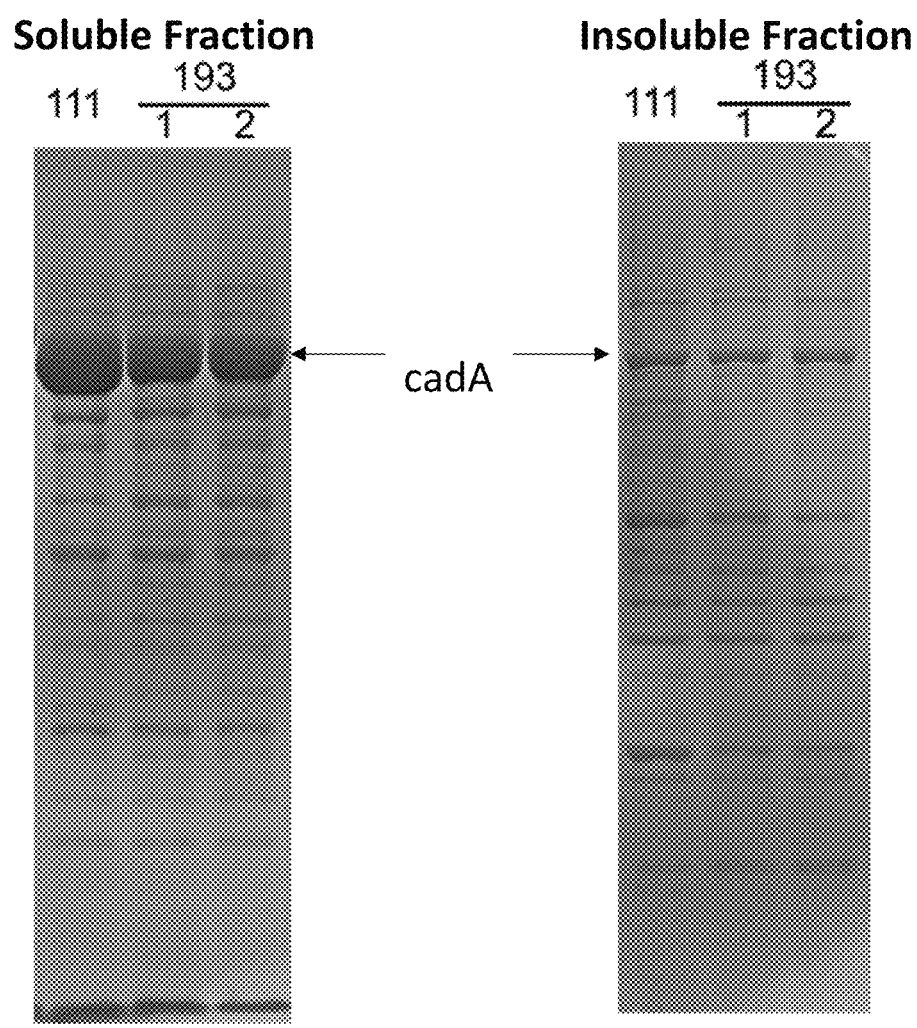

HETEROLOGOUS EXPRESSION OF CARBOHYDRATE BINDING MODULES AND USES THEREOF FOR CADAVERINE PRODUCTION

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "55494_Seqlisting.txt." The Sequence Listing was created on Mar. 17, 2020, and is 80,944 bytes in size. The subject matter of the Sequence Listing is incorporated herein in its entirety by reference.

BACKGROUND OF THE INVENTION

The class of proteins known as acid decarboxylases is a group of enzymes that catalyze the decarboxylase reaction of basic amino acids (e.g., lysine, arginine, ornithine) in order to generate polyamines as part of the acid stress response in many microorganisms. *Escherichia coli* has several pyridoxal phosphate-dependent (PLP)-dependent) acid decarboxylases: CadA, LdcC, AdiA, SpeA, SpeC, SpeF, GadA, and GadB. All of these enzymes function within a narrow pH range, and the enzyme activity decreases significantly outside of that pH range (Kanjee et al., *Biochemistry* 50, 9388-9398, 2011). It has been previously observed that these PLP-dependent decarboxylases dimerize in order to form a complete active site. In some cases, such as CadA, the dimers form decamers that aggregate into higher molecular weight protein complexes required for optimal function. The inhibition of higher molecular weight protein complex formation (e.g., in conditions outside of the optimal pH) leads to a significant decrease in function (Kanjee et al., *The EMBO Journal* 30, 931-944, 2011).

The PLP-dependent decarboxylases that catalyze the conversion of lysine to cadaverine are lysine decarboxylases (e.g., CadA, LdcC, and their homologs). Lysine decarboxylases are of particular interest, because cadaverine can be a platform chemical for the production of various products, such as 1,5-pentamethylene diisocyanate or polyamide 56. However, the production of cadaverine is harmful to the host cell, since cadaverine has been shown to be toxic to cells when present above a certain concentration (Qian et al., *Biotechnol. Bioeng.* 108, 93-103, 2011). Therefore, the temporal control of cadaverine production in order to separate cell growth from the production of the toxic substance is important for achieving high product yields and low production costs.

One method to achieve the temporal control of cadaverine production is by controlling the timing of the expression of the lysine decarboxylase gene using an inducible promoter. An ideal inducible promoter system exhibits no gene expression (and therefore no enzyme production and activity) in the absence of the inducer, and gene expression is turned ON only after the addition of the inducer. This inducible control provides a process that separates the growth phase of the cell from the production of an enzyme whose activity is harmful to the cell. The production of the harmful enzyme after the cell completes its growth phase reduces the toxic effect on the cell, since most toxic effects mainly inhibit cell growth and have less effect on cell function. In some scenarios, an inducible promoter has leaky expression, which means that there is a small amount of expression even in the absence of the inducer. Leaky expression is a problem if the cell is extremely sensitive to the toxic effect of the enzyme.

Alternatively, the most common method to achieve temporal control is to physically separate the lysine production step from the cadaverine production step, so that lysine production is not inhibited by the presence of cadaverine. The cadaverine production step can be achieved in many ways by adding a solution containing lysine to: 1) free cells that heterologously express a lysine decarboxylase gene inside the cell (PCT/CN2014/080873), free cells producing the lysine decarboxylase gene on the cell surface (JP2004298033), immobilized cells producing the lysine decarboxylase protein inside the cell (Bhatia et al., *Bioprocess Biosyst. Eng.* 38, 2315-2322, 2015; Kim et al., *J. Industrial and Eng. Chemistry* 46, 44-48, 2017), free purified or partially purified lysine decarboxylase (Park et al., *J. Microbiol. Biotechnol.* 27, 289-296, 2017), or immobilized lysine decarboxylase proteins (Seo et al, *Process Biochemistry* 51, 1413-1419, 2016).

Processes using cell immobilization have also been reported. Generally, cell immobilization involves either binding the cells to a support or entrapping the cells inside of a matrix. Commonly used materials for the matrix include polyacrylamide, polyurethane, alginate, collagen, and k-carragenan. The binding of a cell to a support is achieved by displaying a polypeptide on the surface of the cell's membrane that enables the cell to bind more strongly to a designated surface. For example, *E. coli* was modified to display catecholamine on its surface, and the engineered cell could bind more strongly to silica and glass microparticles, gold, titanium, silicon, polyethylene terephthalate, polyurethane, and polydimethylsiloxane (Park et al., *Appl. Environ. Microbiol.* 80,43-53, 2014).

Immobilized cells for the production of the amino acids aspartate using chitosan gel (Szymanska et al., *Polish J. Microbiol.* 60, 105-112, 2011), and the amino acid glutamine using carrageenan gel (Amin et al., *World Appl. Sciences J.* 2, 62-67, 2007) have also been proposed. The major challenges in the development and commercialization of an immobilized cell process are productivity and the added cost of the support.

BRIEF SUMMARY OF ASPECTS OF THE DISCLOSURE

In one aspect, the present disclosure presents methods and compositions to immobilize cells overproducing a lysine decarboxylase protein onto a carbohydrate matrix. Carbohydrates (e.g., cellulose, hemicellulose, lignocellulose, xylan, chitin) are a relatively cheap and renewable material. Furthermore, carbohydrate substrates can require little to no modification for immobilization. The embodiments described herein thus provide the ability to maximize the number of times the immobilized cells are reused and reduces the cost of cadaverine production. Furthermore, unlike immobilization of the enzyme, cell lysis or an enzyme recovery step is not required.

In one aspect, the invention is further based, in part, on the surprising discovery that the co-expression of a carbohydrate binding module gene with a lysine decarboxylase gene increases the cell's ability to convert lysine to cadaverine.

In one aspect, provided herein is a host cell genetically modified to express a polynucleotide that encodes a carbohydrate binding module (CBM) fusion polypeptide on the cell surface and to overexpress a lysine decarboxylase, wherein the CBM fusion polypeptide comprises a CBM joined to a surface display polypeptide. In some embodiments, the lysine decarboxylase is exogenous, i.e., it is expressed by a polynucleotide encoding the lysine decarboxylase that is introduced into the host cell. In some embodiments, the host cell is a bacterial host cell. In some embodiments, the CBM is a cellulose binding domain (CBD), which in some embodiments, can be from an exoglucanase, an endoglucanase, a cellulose binding protein, a cellobiohydrolase I or cellobiohydrolase II, a xylanase, or a CipA or CipB inclusion protein. In some embodiments, the CBD is from a xylanase, a cellobiohydrolase I, a cellobiohydrolase II, an exoglucanase, or a cellulose binding protein. In some embodiments, the CBD comprises the amino acid sequence of any one of SEQ ID NOS:13-19. In some embodiments, the surface display polypeptide comprises a region of an outer membrane protein, e.g., OmpA. In some embodiments, the surface display polypeptide comprises amino acids 46-159 of SEQ ID NO:24. In some embodiments, the polynucleotide that encodes the CBM fusion polypeptide comprises a region that encodes a leader peptide that is heterologous to the surface display polypeptide. In some embodiments, the leader peptide is an *Escherichia coli* lipoprotein (Lpp) leader peptide. In some embodiments, the CBM is at the C-terminal end of the fusion polypeptide or within 15 amino acids of the C-terminal end of the fusion polypeptide. In some embodiments, the lysine decarboxylase is CadA or LdcC. In some embodiments, the host cell is from the genus *Escherichia, Hafnia*, or Corynebacteria. In some embodiments, the host cell is an *Escherichia coli, Hafnia alvei*, or *Corynebacterium glutamicum* cell.

In a further aspect, provided herein is a cell culture comprising a host cell as described herein, e.g., in the preceding paragraph. In some embodiments, the cell culture is incubated with a carbohydrate substrate. In some embodiments, the carbohydrate substrate is a cellulose substrate.

In a further aspect, provided herein is a method of producing cadaverine, the method comprising incubating a cell culture comprising a population of host cells with a carbohydrate substrate, wherein the host cell population is genetically modified to express a polynucleotide that encodes a carbohydrate binding module (CBM) fusion polypeptide on the cell surface and to overexpress lysine decarboxylase, under condition in which the CBM fusion polypeptide and the lysine decarboxylase are expressed, wherein the CBM fusion polypeptide comprises a CBM joined to a surface display polypeptide. In some embodiments, the method further comprises isolating the cadverine. In some embodiments, the host cells are bacterial host cells. In some embodiments, the lysine decarboxylase is an exogenous lysine decarboxylase expressed by a polynucleotide that is introduced into the host cell. In some embodiments, the CBM is a cellulose binding domain (CBD), which in some embodiments, can be from an exoglucanase, an endoglucanase, a cellulose binding protein, a cellobiohydrolase I or cellobiohydrolase II, a xylanase, or a CipA or CipB inclusion protein. In some embodiments, the CBD is from a xylanase, a cellobiohydrolase I, a cellobiohydrolase II, an exoglucanase, or a cellulose binding protein. In some embodiments, the CBD comprises the amino acid sequence of any one of SEQ ID NOS:13-19. In some embodiments, the surface display polypeptide comprises a region of an outer membrane protein, e.g., OmpA. In some embodiments, the surface display polypeptide comprises amino acids 46-159 of SEQ ID NO:24. In some embodiments, the polynucleotide that encodes the CBM fusion polypeptide comprises a region that encodes a leader peptide that is heterologous to the surface display polypeptide. In some embodiments, the leader peptide is an *Escherichia coli* lipoprotein (Lpp) leader peptide. In some embodiments, the CBM is at the C-terminal end of the fusion polypeptide or within 15 amino acids of the C-terminal end of the fusion polypeptide. In some embodiments, the lysine decarboxylase is CadA or LdcC. In some embodiments, the host cell population is from the genus *Escherichia, Hafnia*, or Corynebacteria. In some embodiments, the host cells are *Escherichia coli, Hafnia alvei*, or *Corynebacterium glutamicum* cells.

In another aspect, provided herein is a method of obtaining a genetically modified host cell for the production of cadverine, the method comprising: expressing a polynucleotide that encodes a carbohydrate binding module (CBM) fusion polypeptide on the cell surface in a host cell genetically modified to overexpress a lysine decarboxylase, wherein the CBM fusion polypeptide comprises a CBM joined to a surface display polypeptide; and selecting a host cell that produces an increased amount of cadaverine compared to a counterpart host cell that does not overexpress the lysine decarboxylase. In some embodiments, the lysine decarboxylase is an exogenous lysine decarboxylase expressed by a polynucleotide introduced into the host cell. In some embodiments, the host cell is a bacterial host cell. In some embodiments, the CBM is a cellulose binding domain (CBD), which in some embodiments, can be from an exoglucanase, an endoglucanase, a cellulose binding protein, a cellobiohydrolase I or cellobiohydrolase II, a xylanase, or a CipA or CipB inclusion protein. In some embodiments, the CBD is from a xylanase, a cellobiohydrolase I, a cellobiohydrolase II, an exoglucanase, or a cellulose binding protein. In some embodiments, the CBD comprises the amino acid sequence of any one of SEQ ID NOS:13-19. In some embodiments, the surface display polypeptide comprises a region of an outer membrane protein, e.g., OmpA. In some embodiments, the surface display polypeptide comprises amino acids 46-159 of SEQ ID NO:24. In some embodiments, the polynucleotide that encodes the CBM fusion polypeptide comprises a region that encodes a leader peptide that is heterologous to the surface display polypeptide. In some embodiments, the leader peptide is an *Escherichia coli* lipoprotein (Lpp) leader peptide. In some embodiments, the CBM is at the C-terminal end of the fusion polypeptide or within 15 amino acids of the C-terminal end of the fusion polypeptide. In some embodiments, the lysine decarboxylase is CadA or LdcC. In some embodiments, the host cell is from the genus *Escherichia, Hafnia*, or Corynebacteria. In some embodiments, the host cell is an *Escherichia coli, Hafnia alvei*, or *Corynebacterium glutamicum* cell.

DESCRIPTION OF THE FIGURES

FIG. 1 shows an SDS-PAGE of the soluble and insoluble fractions of a *H. avlei* cell culture overexpressing either CadA without a CBD (111) or with a CBD (193).

DETAILED DESCRIPTION OF ASPECTS OF THE DISCLOSURE

Before the present invention is described, it is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and accession numbers mentioned herein are incorporated herein by reference to disclose and describe the methods and/or materials in connection with which the publications are cited.

Terminology

As used herein, "carbohydrate binding module or "CBM" refers to a region of a polypeptide that binds to carbohydrates. Reference to a "CBM" includes a variant, such as a CBM that contains one or more conservative substitutions relative to a naturally occurring CBM sequence, that retains at least 30%, typically at least 50%, at least 80%, or 100%, or greater, of the carbohydrate binding activity of the naturally occurring CBM.

The term "cellulose binding domain" as used herein refers to CBM that binds to cellulose. Reference to a "CBD" includes a variant, such as a CBD that contains one or more conservative substitutions relative to a naturally occurring CBD sequence, that retains at least 30%, typically at least 50%, at least 80%, or 100%, or greater, of the carbohydrate binding activity of the naturally occurring CBD.

As used herein, a "CBM fusion polypeptide" refers to a recombinant polypeptide that comprises a CBM joined to a polypeptide that is expressed on the surface of a cell. The CBM may be directly fused to the cell surface polypeptide or the fusion protein may comprise a peptide linker that joins the CBM to the cell surface polypeptide.

A "CBD fusion polypeptide" as used here refers to a CBM fusion polypeptide in which the carbohydrate binding module is a cellulose binding domain.

A "surface display polypeptide" as used herein refers to a region of a polypeptide that is expressed on the extracellular surface of a microorganism.

The terms "polynucleotide" and "nucleic acid" are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus, the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical" as used here with reference to a polypeptide sequence, refers to a sequence that has at least 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Optimal alignments are typically conducted using BLASTP with default parameters.

Nucleic acid or protein sequences that are substantially identical to a reference sequence include "conservatively modified variants." With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

The term "polypeptide" as used herein includes reference to polypeptides containing naturally occurring amino acids and amino acid backbones as well as non-naturally occurring amino acids and amino acid analogs.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. The following six groups each contain amino acids that further provide illustrative conservative substitutions for one another. 1) Ala, Ser, Thr; 2) Asp, Glu; 3) Asn, Gln; 4) Arg, Lys; 5) Ile, Leu, Met, Val; and 6) Phe, Try, and Trp (see, e.g., Creighton, Proteins (1984)).

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different species). Similarly, a polypeptide is "heterologous" to a host cell if the native wildtype host cell does not produce the polypeptide.

The term "exogenous" refers generally to a polynucleotide sequence or polypeptide that is introduced into a host cell by molecular biological techniques, i.e., engineering to produce a recombinant cell. Examples of "exogenous" polynucleotides include vectors, plasmids, and/or man-made nucleic acid constructs encoding a desired protein. An "exogenous" polypeptide expressed in the host cell may occur naturally in the cell or may be heterologous to the host cell. The term also encompasses progeny of the original host cell that has been engineered to express the exogenous polynucleotide or polypeptide sequence, i.e., a host cell that expresses an "exogenous" polynucleotide may be the original genetically modified host cell or a progeny cell that comprises the genetic modification.

The term "endogenous" refers to naturally-occurring polynucleotide sequences or polypeptides that may be found in a given wild-type cell or organism. In this regard, it is also noted that even though an organism may comprise an endogenous copy of a given polynucleotide sequence or gene, the introduction of an expression construct or vector encoding that sequence, such as to over-express or otherwise regulate the expression of the encoded protein, represents an "exogenous" copy of that gene or polynucleotide sequence. Any of the pathways, genes, or enzymes described herein may utilize or rely on an "endogenous" sequence, which may be provided as one or more "exogenous" polynucleotide sequences, or both.

A host cell that "overexpresses" a lysine decarboxylase refers to a cell that has a genetic modification to overexpress a lysine decarboxylase, e.g., comprises an expression construct that encodes an exogenous lysine decarboxylase. The lysine decarboxylase may be a lysine decarboxylase that is naturally occurs in the wildtype cell or may be a lysine decarboxylase from another organism. In some embodiments, a cell that "overexpresses" a lysine decarboxylase expresses an amount of protein at least 10%, at least 25%, at least 50%, or at least 100% or greater, than that produced by the wildtype counterpart cell of the same strain that does not have the genetic modification.

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence can have two or more sequences from unrelated genes arranged to make a new functional nucleic acid.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide is introduced into a host cell and is targeted to a position in the genome of the host cell such that expression of the polynucleotide sequence is driven by a promoter that is present in the host cell.

The term "host cell" as used in the context of this invention refers to a microorganism and includes an individual cell or cell culture that can be or has been a recipient of any recombinant vector(s) or isolated polynucleotide(s) of as described herein. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

The term "isolated" refers to a material that is substantially or essentially free from components that normally accompany it in its native state. For example, an "isolated polynucleotide," as used herein, may refer to a polynucleotide that has been isolated from the sequences that flank it in its naturally-occurring or genomic state, e.g., a DNA fragment that has been removed from the sequences that are normally adjacent to the fragment, such as by cloning into a vector. A polynucleotide is considered to be isolated if, for example, it is cloned into a vector that is not a part of the natural environment, or if it is artificially introduced in the genome of a cell in a manner that differs from its naturally-occurring state. Alternatively, an "isolated peptide" or an "isolated polypeptide" and the like, as used herein, may refer to a polypeptide molecule that is free of other components of the cell, i.e., it is not associated with in vivo cellular substances.

The invention employs various routine recombinant nucleic acid techniques. Generally, the nomenclature and the laboratory procedures in recombinant DNA technology described below are commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2016).

Carbohydrate Binding Modules

There are at least 64 families of CBMs that have been identified, and are described in the CAZy database (Cantarel et al., Nuc. Ac. Res. 37, D233-D238, 2009). Cellulose-binding-domains polypeptides are well studied as part of the cellulase system (cellulosome) used by some microorganisms to degrade cellulose into disaccharides and monosaccharides. There are at least 180 different CBDs that are categorized into 13 families (Carrard et al., PNAS 97, 10342-10347, 2000). Most CBDs fall into one of three families. Family I CBDs are found only in fungi and range in size from 32-36 amino acids. Family II CBDs are found more diversely, and can range in size from 90-100 amino acids. Family III CBDs are also found more diversely, and can range in size from 130-172 amino acids. A review of CBMs and their applications is provided in Shoseyov et al., Microbiol. Mol. Biol. Reviews 70, 283-295, 2006.

In nature, a CBM is often located at either the N terminus or C terminus of the polypeptide, but may also be found in a middle region, rather than the end of a polypeptide. For example, the CBM of the cellobiohydralase I protein from Trichoderma reesei (crystal structure available under protein database accession number PDB ID: 10EL) is located at the C-terminus, while the CBM of the cellobiohydralase II protein from T. reesei (structure available under accession number PDB ID: 3CBH) is located at the N-terminus. The CBD of CipA (see, the following paragraph) is contained in the middle of protein. Other microorganisms known to express enzymes that contain CBMs include Trichoderma viridae, Cellomonas fimi, Cellvibrio mixtus, Cellvibrio japonicus, Clostridium thermocellum, Piromyces equi, Penicillium funiculosum, Arthrobacter globiformis, Aspergillus kawachii, Pseudomonas cellulose, Phanerochaete chrysosporium, Paenibacillus sp. Meloidogyne, Agaricus bisporus, Thermotoga maritima, Humicola grisea, and Humicola insolens.

CBMs can bind either reversibly or irreversibly to their substrate. For example, the CBM of cellobiohydrolase I and cellobiohydrolase II of T. reesei both bind irreversibly to cellulose (Carrard & Linder, Eur. J. Biochem. 262, 637-643, 1999). However, the CBM of the CipA protein of Cellomonas fimi binds reversibly to cellulose (Yaron et al., in Genetics, Biochemistry and Ecology of Cellulose Degradation: Mie Biofbrum 98, eds. Ohmiya et al., pp 45-46, 1998).

The crystal structures of various CBDs have been solved. For example, the T. reesei cellobiohydrolase I CBD belongs to Family I, and is composed of a wedge-shaped irregular beta-sheet, where one side of the molecule consists of three conserved tyrosine residues and forms a hydrophobic planar surface that is able to bind cellulose. The C. fimi beta-1,4-glycanase CBD belongs to Family II. It is composed of an elongated, nine-stranded beta-barrel, where one side of the barrel has three solvent-exposed tryptophans in addition to other hydrophilic residues that bind the carbohydrate substrate. The Clostridium thermocellum Cip CBD belongs to Family III, and consists of a nine-stranded beta-sandwich jelly roll with a surface exposed planar linear strip of aromatic and polar residues that interact with the cellulose surface (Tormo et al., The EMBO J. 15, 5739-5751, 1996). Throughout Families I, II, and III, the CBDs in general exhibit a flat protein surface moiety that includes two or more conserved solvent-exposed aromatic residues that are able to interact with the carbohydrate substrate.

In some embodiments, a CBD fusion polypeptide of the present invention comprises a CBD, or functional variant thereof, from C. fimi exoglucanase, Accession No. AEA30147.1 (SEQ ID: 1); C. fimi cellulose binding protein, Accession No. WP013770490.1 (SEQ ID: 3); Clostridium thermocellum CipA, Accession No. CCV01467.1 (SEQ ID: 5); C. thermocellum CipB, (Accession No. Q01866.1 (SEQ ID: 6); T. reesei cellobiohydrolase I, Accession No. P62694.1 (SEQ ID: 7); T. reesei cellobiohydrolase II, Accession No. P07987.1 (SEQ ID: 9); or Cellvibrio japonicus XynA, Accession No. P14768.2 (SEQ ID: 11).

In some embodiments, a CBD fusion polypeptide of the present invention comprises a CBD, or functional variant thereof, from C. fimi exoglucanase, Accession No. AEA30147.1 (SEQ ID: 1); C. fimi cellulose binding protein, Accession No. WP013770490.1 (SEQ ID: 3); T. reesei cellobiohydrolase I, Accession No. P62694.1 (SEQ ID: 7); T. reesei cellobiohydrolase II, Accession No. P07987.1 (SEQ ID: 9); or Cellvibrio japonicus XynA, Accession No.

P14768.2 (SEQ ID: 11). Of these five enzymes, the CBDs of *C. fimi* exoglucanase, *C. fimi* cellulose binding protein, and *T. reesei* cellobiohydrolase I are located at the C terminus. The CBD of *C. fimi* exoglucanase is annotated as amino acid residues 383-482, the CBD of *C. fimi* cellulose binding protein is annotated as amino acid residues 266-352, and the CBD of *T. reesei* cellobiohydrolase I is annotated as amino acids 481-513. In contrast, the CBDs of *T. reesei* cellobiohydrolase II and *C. japonicus* XynA are located at the N terminus. The CBD of *T. reesei* cellobiohydrolase II is annotated as amino acids 30-62, and the CBD of *C. japoniucs* XynA is annotated as amino acids 29-125.

In some embodiments a CBD that is contained in a CBD fusion polypeptide of the present invention belongs to Family I or Family II. For example, *T. reesei* cellobiohydrolase I and *T. reesei* cellobiohydrolase II both contain CBDs that belong to Family I, while the *C. fimi* exoglucanase, *C. fimi* cellulose binding protein, and *C. japonicus* XynA contain CBDs that belong to Family II.

In some embodiments, a CBD fusion polypeptide of the present invention comprises a CBD from a cellobiohydrolase, e.g., cellobiohydrolase I or II from *T. reesei*, cellobiohydrolase II from *T. harzianum*; a CBD from an exoglucanase, e.g., endo-1,4 glucanase from *B. subtilis*; or a CBD from an exoglucanase, e.g., TEX1 from *T. viride*.

In some embodiments, a CBD or CBM fusion polypeptide comprises a biologically active variant of a naturally occurring CBD or CBM sequence. Biologically active variants include alleles, mutants, fragments, and interspecies homologs of specific CBD or CBM polypeptides described herein that bind carbohydrate. In some embodiments, a CBM or CBD has at least 65% amino acid sequence identity, and in some embodiments at least 70%, 75%, 80%, 85%, 90% identity; often at least 91%, 92%, 93%, 94%, 95%, 96%, 97%, 98% or 99% or greater amino acid sequence identity, to a naturally occurring CBM or CBD sequence. In some embodiments, a CBD has at least 65% amino acid sequence identity, or in some embodiments, at least 70%, 75%, 80%, 85%, 90%, 91%, 92%, 93%, 94%, 95%, 96%, 97%, 98% or 99% or greater, amino acid sequence identity to any one of SEQ ID NOS:13 to 19. In some embodiments, a biologically active CBM or CBD variant polypeptide may comprise one or more deletions relative to a naturally occurring CBD amino acid sequence, so long as the CBD retains activities. In some embodiments, 1, 2, 3, 4, or 5 amino acids may be deleted, e.g., from the N-terminal and/or C-terminal end of a family II CBD, relative to the naturally occurring family II CBD amino acid sequence. In some embodiments, 1 or 2, or 1, 2, or 3, amino acids may be deleted, e.g., from the N-terminal and/or C-terminal end of a family I CBD, relative to the naturally occurring family I CBD amino acid sequence. In some embodiments, the CBD regions of a fusion polypeptide of the invention may comprise additional amino acids at the N-terminal and/or C-terminal end, e.g., from the native protein in which the CBD occurs. In some embodiments, a fusion polypeptide of the invention may comprise more than one CBD regions, which may be the same or different.

Carbohydrate binding activity of a CBD, e.g., cellulose binding activity, can be tested directly or can be tested indirectly, e.g., by measuring a downstream endpoint such as cadaverine production as illustrated in the examples. Carbohydrate binding activity can also be directly measured by taking advantage of the solvent exposed aromatic residues that characterizes most CBDs. For example, a solution containing carbohydrate binding activity can be exposed to cellulose, and the change in the amount of fluorescence in solution could be measured in order to determine the amount of binding activity present. Fluorescence measurements can be based on the change in the amount of exposed tyrosine residues (excitation 274 nm/emission 303 nm), phenylalanine residues (excitation 257 nm/emission 282 nm), or tryptophan residues (excitation 280 nm/emission 348 nm) left in solution before and after exposure to cellulose. A biologically active CBD variant typically has at least 30%, at least 50%, at least 75%, or greater, of the binding activity of the naturally occurring CBD.

Cell Surface Display Proteins

A fusion polypeptide of the present invention further comprises a region that targets the CBM or CBD for expression on the cell surface. Such a region is also referred to herein as a display polypeptide. Cell surface display systems found in various microorganisms have been well described and can be categorized into seven types: outer membrane proteins (e.g., OmpA, OmpC, LamB, and FhuA), cell surface appendages (e.g., flagella, pili, fimbriae), lipoprotein-derived (Lpp), virulence factors-based (e.g., EaeA inimin), Tat-dependent, autotransporter-dependent (*Neisseria* IgA, *E. coli* AIDA-I), and ice nucleating protein-based (*P. syringiae* Inp or InaV) (Chen & Georgiou, Biotechnol. and Bioeng. 79, 496-503, 2002). These different systems and their applications are reviewed in Bloois et al., *Trends in Biotechnol.* 29, 79-86, 2011. In addition, a combination of two or more of the above systems can also be used to display a protein on the surface of a cell. For example, a CBM or CBD fusion polypeptide of the present invention may contain an *E. coli* lipoprotein Lpp with a fragment of the *E. coli* outer membrane protein (Georgiou et al., *Protein Eng.* 9, 239-247, 1996).

In some embodiments, a CBM or CBD fusion polypeptide of the present invention comprises a leader polypeptide that is heterologous to the display polypeptide. Thus, for example, in some embodiments, the display polypeptide sequence may be from an Omp polypeptide such as an OmpA polypeptide, or an alternative Omp polypeptide, while the leader peptide is from a heterologous protein.

The fusion polypeptide may be configured such that the CBM or CBD is at or near, e.g., within 10 or 15 amino acids, of the end, e.g., the C-terminal end, of the cell surface display polypeptide so long as the CBM or CBD is displayed on the cell surface. In some embodiments, a CBM or CBD fusion polypeptide may contain the carbohydrate binding domain in the middle of the protein or a region that is greater than 15 amino acids from the end of the cell surface protein, so long as the CBM or CBD is displayed on the cell surface. In some embodiments, the fusion polypeptide may comprise a peptide linker, e.g., a flexible linker, which typically comprise small, nonpolar or polar amino acids such as Gly, Asn, Ser, Thr, Ala, and the like, joining the carbohydrate binding domain sequence to the display protein sequence.

Nucleic Acids Encoding CBM or CBD Fusion Polypeptides

Isolation or generation of CBD polynucleotide sequences and for incorporation to a fusion polypeptide that comprises a CBD joined to a cell surface display polypeptide can be accomplished by a number of techniques. In some embodiments, oligonucleotide probes based on the sequences disclosed here can be used to identify the desired polynucleotide in a cDNA or genomic DNA library from a desired bacteria species. Alternatively, the nucleic acids of interest are amplified from nucleic acid samples using routine amplification techniques. For instance, PCR may be used to amplify the sequences of the genes directly from mRNA, from cDNA, from genomic libraries or cDNA libraries. Appropriate primers and probes for identifying a CBD-containing polynucleotide in bacteria can be generated based on known parameters. Illustrative primer sequences are shown in the Table of Primers in the Examples section. Although obtaining a polynucleotide that encodes a desired polypeptide is illustrated in this paragraph with reference to CBD domains, it is understood that a polynucleotide encoding any polypeptide of interest, e.g., a surface display polypeptide, a leader peptide, or a lysine decarboxylase polypeptide, can be obtained using the same techniques.

Nucleic acid sequences encoding a CBM or CBD fusion polypeptide and/or a lysine decarboxylase polypeptide, may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See e.g., Henaut and Danchin in "*Escherichia coli* and *Salmonella*," Neidhardt, et al. Eds., ASM Pres, Washington D.C. (1996), pp. 2047-2066; *Nucleic Acids Res.* 20:2111-2118; Nakamura et al., 2000, *Nucl. Acids Res.* 28:292).

Preparation of Recombinant Vectors

Recombinant vectors for expression of a CBM or CBD fusion polypeptide can be prepared using methods well known in the art. For example, a DNA sequence encoding the fusion polypeptide, can be combined with transcriptional and other regulatory sequences which will direct the transcription of the sequence from the gene in the intended cells, e.g., bacterial cells such as *H. alvei*, *E. coli*, or *C. glutamicum*. In some embodiments, an expression vector that comprises an expression cassette that comprises the gene encoding the CBM or CBD fusion polypeptide further comprises a promoter operably linked to the nucleic acid sequence encoding the polypeptide. In other embodiments, a promoter and/or other regulatory elements that direct transcription of the polynucleotide encoding a CBM or CBD fusion polypeptide are endogenous to the host cell and an expression cassette comprising a gene that encodes the fusion polypeptide is introduced, e.g., by homologous recombination, such that the exogenous gene is operably linked to an endogenous promoter and expression is driven by the endogenous promoter.

As noted above, expression of the polynucleotide encoding CBM or CBD fusion polypeptide can be controlled by a number of regulatory sequences including promoters, which may be either constitutive or inducible; and, optionally, repressor sequences, if desired. In some embodiments, the promoter is a constitutive promoter. Examples of suitable promoters, especially in a bacterial host cell, are the promoters obtained from the *E. coli* lac operon and other promoters derived from genes involved in the metabolism of other sugars, e.g., galactose and maltose. Additional examples include promoters such as the trp promoter, bla promoter bacteriophage lambda PL, and T5. In addition, synthetic promoters, such as the tac promoter (U.S. Pat. No. 4,551,433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra. Additional promoters include promoters described by Jensen & Hammer, *Appl. Environ. Microbiol.* 64:82, 1998; Shimada, et al., *J. Bacteriol.* 186:7112, 2004; and Miksch et al., *Appl. Microbiol. Biotechnol.* 69:312, 2005.

In some embodiments, a promoter that influences expression of a gene encoding a fusion polypeptide of the invention may be modified to increase expression. For example, an endogenous promoter may be replaced by a promoter that provides for increased expression compared to the native promoter.

An expression vector may also comprise additional sequences that influence expression of a polynucleotide encoding the fusion polypeptide. Such sequences include enhancer sequences, a ribosome binding site, or other sequences such as transcription termination sequences, and the like.

A vector expressing a polynucleotide encoding a fusion polypeptide of the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism, e.g., a bacterial cell such as *E. coli*, *H. alvei*, or *C. glutamicum*.

Although any suitable expression vector may be used to incorporate the desired sequences, readily available bacterial expression vectors include, without limitation: plasmids such as pSC101, pBR322, pBBR1MCS-3, pUR, pET, pEX, pMR100, pCR4, pBAD24, p15a, pACYC, pUC, e.g., pUC18 or pUC19, or plasmids derived from these plasmids; and bacteriophages, such as M13 phage and λ phage. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

Host Cells

The present invention provides for a genetically modified host cell that is engineered to express a CBM or CBD fusion polypeptide of the invention in which the host cell is also engineered to overexpress a lysine decarboxylase polypeptide, e.g., an exogenous lysine decarboxylase.

In some embodiments, a genetically modified host cell that expresses a CBM or CBD fusion polypeptide expresses is modified to express a heterologous lysine decarboxylase. As used herein, a lysine decarboxylase refers to an enzyme that converts L-lysine into cadaverine. The term includes variants of native, i.e., naturally occurring, lysine decarboxylase enzymes that have lysine decarboxylase enzymatic activity. Lysine decarboxylases are classified as E.C.

4.1.1.18. Lysine decarboxylase polypeptides are well characterized enzymes, the structures of which are well known in the art (see, e.g., Kanjee, et al., EMBO J. 30: 931-944, 2011; and a review by Lemmonier & Lane, Microbiology 144; 751-760, 1998; and references described therein). Illustrative lysine decarboxylase sequences are CadA homologs from *Klebsiella* sp., WP 012968785.1; *Enterobacter aerogenes*, YP 004592843.1; *Salmonella enterica*, WP 020936842.1; *Serratia* sp., WP 033635725.1; and *Raoultella ornithinolytica*, YP 007874766.1; and LdcC homologs from *Shigella* sp., WP 001020968.1; *Citrobacter* sp., WP 016151770.1; and *Salmonella enterica*, WP 001021062.1. In some embodiments, the lysine decarboxylase polypeptide expressed is the wild-type Ldc2 from *Pseudomonas aeruginosa*, or a mutant of such a polypeptide as described in PCT/CN2014/080873. In some embodiments, the lysine decarboxylase polypeptide expressed is the wild-type Ldc from *Klebsiella oxytoca*, or a mutant of such a polypeptide as described in (PCT/CN2015/071978).

In some embodiments, a genetically modified host cell that expresses a CBM or CBD fusion polypeptide is genetically modified host cell to express a heterologous CadA or heterologous LdcC.

In some embodiments, a genetically modified host cell that overexpresses a lysine decarboxylase comprises a modification in a regulatory sequence, e.g., a promoter, in the gene encoding an endogenous lysine decarboxylase that results in higher expression levels of the endogenous lysine decarboxylase. For example, the endogenous promoter may be replaced by an alternative promoter that provides for higher expression levels compared to the native promoter sequence, and/or regulatory sequences can be modified, e.g., repressor sequences or inducible sequences can be inactivated, to increase expression compared to the counterpart cell of the same strain that does not have the modification.

In some aspects, genetic modification of a host cell to express a CadA variant polypeptide is performed in conjunction with modifying the host cell to overexpress one or more lysine biosynthesis polypeptides.

In some embodiments, a host cell may be genetically modified to express one or more polypeptides that affect lysine biosynthesis. Examples of lysine biosynthesis polypeptides include the *E. coli* genes SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes involved in cadaverine production. Illustrative genes encoding lysine biosynthesis polypeptides are provided below.

| Protein | Gene | EC Number | GenBank Accession No. |
|---|---|---|---|
| α-ketogultarate dehydrogenase (SucA) | sucA | 1.2.4.2 | YP_489005.1 |
| Phosphoenolpyruvate carboxylase (PPC) | ppc | 4.1.1.31 | AAC76938.1 |
| aspartate transaminase (AspC) | aspC | 2.6.1.1 | AAC74014.1 |
| aspartate kinase (LysC) | lysC | 2.7.2.4 | NP_418448.1 |
| aspartate semialdehyde dehydrogenase (Asd) | asd | 1.2.1.11 | AAC76458.1 |
| dihydrodipicolinate synthase (DapA) | dapA | 4.3.3.7 | NP_416973.1 |
| dihydropicolinate reductase (DapB) | dapB | 1.17.1.8 | AAC73142.1 |
| tetrahydrodipicoinate succinylase (DapD) | dapD | 2.3.1.117 | AAC73277.1 |
| N-succinyldiaminopimelate aminotransferase (ArgD) | argD | 2.6.1.11 | AAC76384.1 |
| N-succinyl-L-diaminopimelate deacylase (DapE) | dapE | 3.5.1.18 | AAC75525.1 |
| diaminopimelate epimerase (DapF) | dapF | 5.1.1.7 | AAC76812.2 |
| diaminopimelate decarboxylase (LysA) | lysA | 4.1.1.20 | AAC75877.1 |
| meso-diaminopimelate dehydrogenase (Ddh) | ddh | NA | P04964.1 |
| pyridine nucleotide transhydrogenase (PntAB) | pntAB | NA | AAC74675.1, AAC74674.1 |
| cytochrome O oxidase (CyoABE) | cyoABE | 1.10.3.10 | AAC73535.1, AAC73534.1, AAC73531.1 |
| glutamate decarboxylase (GadAB) | gadAB | 4.1.1.15 | AAC76542.1, AAC74566.1 |
| L-amino acid efflux transporter (YbjE) | ybjE | NA | AAC73961.2 |
| glutamate dehydrogenase (GdhA) | gdhA | 1.4.1.4 | AAC74831.1 |
| citrate synthase (GltA) | gltA | 2.3.3.1/ 2.3.3.16 | AAC73814.1 |
| succinyl-coA synthase (SucC) | sucC | 6.2.1.5 | AAC73822.1 |
| glutamate-GABA antiporter (GadC) | gadC | NA | AAC74565.1 |
| aconitase B (AcnB) | acnB | 4.2.1.99 | AAC73229.1 |
| pyruvate-formate lyase (PflB) | pflB | NA | AAC73989.1 |
| aspartate kinase/homoserine dehydrogenase (ThrA) | thrA | 2.7.2.4 | AAC73113.1 |
| isocitrate lyase (AceA) | aceA | 4.1.3.1 | AAC76985.1 |
| malate synthase (AceB) | aceB | 2.3.3.9 | AAC76984.1 |
| glutmate synthase (GltB) | gltB | 1.4.1.13 | AAC76244.2 |
| pyruvate dehydrogenase (AceE) | aceE | 1.2.4.1 | AAC73225.1 |
| succinate dehydrogenase (SdhA) | sdhA | 1.3.5.1 | AAC73817.1 |
| UDP-N-acetylmuramoyl-L-alanyl-D-glutamate: meso-diaminopimelate ligase (MurE) | murE | 6.3.2.13 | AAC73196.1 |
| putrescine/cadaverine aminopropyltransferase (SpeE) | speE | 2.5.1.16 | AAC73232.1 |
| spermidine acetyltransferase (SpeG) | speG | NA | AAC74656.1 |
| glutamate-putrescine/glutamate-cadaverine ligase (PuuA) | puuA | NA | AAC74379.2 |
| putrescine importer (PuuP) | puuP | NA | AAC74378.2 |
| putrescine/cadaverine aminotransferase (YgjG) | ygjG | 2.6.1.82 | AAC76108.3 |

In some embodiments, a host cell may be genetically modified to attenuate or reduce the expression of one or more polypeptides that affect lysine biosynthesis. Examples of such polypeptides include the *E. coli* genes Pck, Pgi, DeaD, CitE, MenE, PoxB, AceA, AceB, AceE, RpoC, and ThrA, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes attenuated to increase cadaverine production. Illustrative genes encoding polypeptides whose attenuation increases lysine biosynthesis are provided below.

| Protein | Gene | EC Number | GenBank Accession No. |
|---|---|---|---|
| PEP carboxykinase (Pck) | pck | 4.1.1.49 | NP_417862 |
| Glucose-6-phosphate isomerase (Pgi) | pgi | 5.3.1.9 | NP_418449 |
| DEAD-box RNA helicase (DeaD) | deaD | | NP_417631 |
| citrate lyase (CitE) | citE | 4.1.3.6/ 4.1.3.34 | NP_415149 |
| o-succinylbenzoate-CoA ligase (MenE) | menE | 6.2.1.26 | NP_416763 |
| pyruvate oxidase (PoxB) | poxB | 1.2.2.2 | NP_415392 |
| isocitrate lyase (AceA) | aceA | 4.1.3.1 | NP_418439 |
| malate synthase A (AceB) | aceB | 2.3.3.9 | NP_418438 |
| pyruvate dehydrogenase (aceE) | aceE | 1.2.4.1 | NP_414656 |
| RNA polymerase b' subunit (RpoC) | rpoC | 2.77.6 | NP_418415 |
| aspartokinase I (ThrA) | thrA | 2.7.2.4/ 1.1.1.3 | NP_414543 |

A host cell engineered to express a CBM or CBD fusion polypeptide that is expressed on the surface of the host cell is typically a bacterial host cell. In typical embodiments, the bacterial host cell is a Gram-negative bacterial host cell. In some embodiments of the invention, the bacterium is an enteric bacterium. In some embodiments of the invention, the bacterium is a species of the genus *Corynebacterium, Escherichia, Pseudomonas, Zymomonas, Shewanella, Salmonella, Shigella, Enterobacter, Citrobacter, Cronobacter, Erwinia, Serratia, Proteus, Hafnia, Yersinia, Morganella, Edwardsiella,* or *Klebsiella* taxonomical classes. In some embodiments, the host cells are members of the genus *Escherichia, Hafnia,* or *Corynebacterium*. In some embodiments, the host cell is an *Escherichia coli, Hafnia alvei,* or *Corynebacterium glutamicum* host cell. In some embodiments, the host cell is *Escherichia coli*. In some embodiments, the host cell is *Hafnia alvei*. In some embodiments, the host cell is *Corynebacterium glutamicum*.

In some embodiments, the host cell is a gram-positive bacterial host cell, such as a *Bacillus* sp., e.g., *Bacillus subtilis* or *Bacillus licheniformis*; or another *Bacillus* sp. such as *B. alcalophilus, B. aminovorans, B. amyloliquefaciens, B. caldolyticus, B. circulans, B. stearothermophilus, B. thermoglucosidasius, B. thuringiensis* or *B. vulgatis*.

In some embodiments, a host cell modified in accordance with the invention is yeast genetically modified to express a CBD or CBM fusion polypeptide comprising a carbohydrate binding domain fused to cell surface display polypeptide and to overexpress a lysine decarboxylase. Illustrative yeasts include species selected from *Saccharomyces* spp., such as *Sacharomyces cerevisiae; Schizosaccharomyces* spp. such as *Schizosaccharomyces pombe, Kluyveromyces* spp. such as *Kluyveromyces lactis* or *Kluyveromyces marxianus; Pichia* spp., such as *Pichia pastoris; Yarrowia* spp., *Candida* spp., *Hansenula* spp. and the like. In some embodiments, the host cell is a cyanobacteria or filamentous fungi, such as an *Aspergilluis* spp. As understood in the art, the cell surface display polypeptide is selected based on the host cell that is modified. For example, for yeast, a display polypeptide that is displayed on the surface of a yeast cell is selected for generating the fusion polypeptide.

Host cells modified in accordance with the invention can be screened for increased production of cadaverine, as described herein.
Methods of Producing Cadaverine.

A host cell genetically modified to express a CBD or CBM fusion polypeptide comprising the carbohydrate binding domain fused to cell surface display polypeptide, e.g., at the carboxyl end or N-terminal end, that further overexpresses a lysine decarboxylase, e.g., an exogenous lysine decarboxylase, such as CadA, provides a higher yield of cadaverine relative to a counterpart host cell, which does not express the fusion polypeptide, but is otherwise of the same genetic background. In some embodiments, cadaverine production is improved by at least 5%, typically at least 10%, 15% 20%, 30%, 40%, 50%, 60%, 70%, 80%, 90%, 100%, or greater compared to the counterpart host cell. In some embodiments, conversion of lysine to cadaverine can be measured using NMR by sampling the amount of lysine converted in the presence of PLP into cadaverine at regular intervals, e.g., about every 1.5 minutes for a total of 20 minutes, and taking the slope of the linear portion of the yield curve.

Host cells modified to co-express a CBM or CBD fusion polypeptide on the cell surface and a lysine decarboxylase gene may be immobilized to a carbohydrate substrate. Thus, a host cell that expresses a CBD fusion polypeptide may be immobilized on a cellulose substrate. For example, cell cultures may be incubated with a cellulose substrate such as beads or filter paper, or other inert substrates that contain cellulose. Additional examples of carbohydrate immobilization materials include Avicel, acid-swollen cellulose, bacterial microcrystalline cellulose, cellulose filter paper (e.g., Whatman No. 1 filter paper), cellulose fabric (e.g., Bemliese 606), chitin beads, or chitin flakes.

Cadaverine can them be isolated and/or converted to a desired product, using well known methods.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

Example 1: Construction of Plasmid Vectors that Encode CadA

A plasmid vector containing wild-type *E. coli* cadA (SEQ ID NO:21), which encodes the lysine decarboxylase CadA (SEQ ID NO:20), was amplified from the *E. coli* MG1655 K12 genomic DNA using the PCR primers cadA-F and cadA-R, digested using the restriction enzymes SacI and XbaI, and ligated into pUC18 to generate the plasmid pCIB60. The 5' sequence upstream of the cadA gene was optimized using the PCR primers cadA-F2 and cadA-R2 to create pCIB71. The kanamycin resistance gene npt was amplified using the primers npt-F and npt-R, and cloned behind cadA in pCIB71 to create pCIB111.

Example 2: Construction of a Plasmid Vector Expressing a Surface Display Sequence lpp-ompA A polypeptide that can target a protein fused to its C terminal end to the outer membrane of a Gram-negative bacteria can consist of the leader peptide of the Lpp lipoprotein and a portion of the transmembrane domain of OmpA (Georgiou et al., *Protein Eng.* 9, 239-247, 1996). The nucleotide sequence encoding the first 29 amino acid residues of *E. coli* Lpp was amplified using the primers lpp-F1 and lpp-R1, and fused to the nucleotide sequence encoding the amino acid residues 46-159 of *E. coli* OmpA amplified using the primers lpp-ompA-F and ompA-R. The fusion polypeptide fragment was digested using the restriction enzymes SacI and XbaI, and ligated into pUC18 to generate the plasmid pCIB129. The 5' sequence upstream of the lpp gene fragment was optimized using the PCR primers lpp-F2 and lpp-R2 to create pCIB143.

Example 3: Construction of a Plasmid Vector Expressing the CBD from Cellvibrio japonicas XynA The amino acid sequence of XynA from *C. japonicus* was obtained from NCBI (GenBank ID P14768.2) (SEQ ID NO:11). The portion of the protein sequence that includes the XynA CBD was codon optimized (SEQ ID NO:12) for heterologous expression in *E. coli*. Codon optimization and DNA assembly was performed according to Hoover D M & Lubkowski J, *Nucleic Acids Research* 30:10, 2002. The synthesized DNA product was amplified with the PCR primers XynA-F and XynA-R, digested using the restriction enzymes XbaI and SphI, and ligated into pCIB143 to create plasmid pCIB147.

Example 4: Construction of a Plasmid Vector Expressing the CBD from Trichoderma reesei Cellobiohydrolase I The amino acid sequence of cellobiohydrolase I (CBH1) from *T. reesei* was obtained from NCBI (GenBank ID P62694.1) (SEQ ID NO:7). The portion of the protein sequence that includes the CBH1 CBD was codon optimized (SEQ ID NO:8) for heterologous expression in *E. coli*. Codon optimization and DNA assembly was performed according to Hoover D M & Lubkowski J, *Nucleic Acids Research* 30:10, 2002. The synthesized DNA product was amplified with the PCR primers CBH1-F and CBH1-R, digested using the restriction enzymes XbaI and SphI, and ligated into pCIB143 to create plasmid pCIB150.

Example 5: Construction of a Plasmid Vector Expressing the CBD from Trichoderma reesei Cellobiohydrolase II The amino acid sequence of cellobiohydrolase II (CBH2) from *T. reesei* was obtained from NCBI (GenBank ID P07987.1) (SEQ ID NO:9). The portion of the protein sequence that includes the CBH2 CBD was codon optimized (SEQ ID NO:10) for heterologous expression in *E. coli*. Codon optimization and DNA assembly was performed according to Hoover D M & Lubkowski J, *Nucleic Acids Research* 30:10, 2002. The synthesized DNA product was amplified with the PCR primers CBH2-F and CBH2-R, digested using the restriction enzymes XbaI and SphI, and ligated into pCIB143 to create plasmid pCIB151.

Example 6: Construction of a Plasmid Vector Expressing the CBD from Cellomonas fimi Exoglucanase The amino acid sequence of exoglucanase from *C. fimi* was obtained from NCBI (GenBank ID AEA30147.1) (SEQ ID NO:1). The portion of the protein sequence that includes the exoglucanase CBD was codon optimized (SEQ ID NO:2) for heterologous expression in *E. coli*. Codon optimization and DNA assembly was performed according to Hoover D M & Lubkowski J, *Nucleic Acids Research* 30:10, 2002. The synthesized DNA product was amplified with the PCR primers CEX-F and CEX-R, digested using the restriction enzymes XbaI and SphI, and ligated into pCIB143 to create plasmid pCIB158.

Example 7: Construction of a Plasmid Vector Expressing the CBD from Cellomonas fimi Cellulose Binding Protein The amino acid sequence of cellulose binding protein from *C. fimi* was obtained from NCBI (GenBank ID WP013770490.1) (SEQ ID NO:3). The portion of the protein sequence that includes the cellulose binding protein CBD was codon optimized (SEQ ID NO:4) for heterologous expression in *E. coli*. Codon optimization and DNA assembly was performed according to Hoover D M & Lubkowski J, *Nucleic Acids Research* 30:10, 2002. The synthesized DNA product was amplified with the PCR primers CCBP-F and CCBP-R, digested using the restriction enzymes XbaI and SphI, and ligated into pCIB143 to create plasmid pCIB161.

Example 8: Construction of Plasmid Vectors Co-Expressing Genes that Encode a CBD and a Lysine Decarboxylase The cadA and npt genes were amplified from pCIB111 using the primers cadA-F3 and npt-R, while removing the SphI restriction site in the npt gene using SOEing (Splicing by Overlapping Extension) PCR with the primers npt-F2 and npt-R2. The PCR fragment was digested using the restriction enzymes SphI and NdeI, and ligated into pCIB147, pCIB150, pCIB151, pCIB158, and pCIB161 in order to create the plasmids pCIB171, pCIB193, pCIB190, pCIB196, and pCIB176, respectively.

Example 9: Production of Cadaverine from Free Cells of E. coli Co-Overexpressing Genes that Encode a CBD and Lysine Decarboxylase

*E. coli* was transformed with pCIB111, pCIB171, pCIB176, pCIB190, pCIB193, or pCIB196. Three single colonies from each transformation were grown overnight at 37° C. in 4 mL of LB medium with kanamycin (50 µg/mL). The following day, 0.6 mL of each overnight culture was added to 0.4 mL of lysine-HCl and PLP to a final concentration of 160 g/L and 0.1 mM, respectively. Each mixture was incubated at 37° C. for 4 hours. Cadaverine production from each sample was quantified using NMR, and yield was calculated by dividing the molar amount of cadaverine produced by the molar amount of lysine added. The yield from each sample after 4 hours is presented in Table 1.

TABLE 1

Production of cadaverine by *E. coli* strains overproducing a CBD and a lysine decarboxylase.

| Strain | Plasmid | Cadaverine Yield (%) |
| --- | --- | --- |
| *E. coli* | pCIB111 | 55.8 ± 3.5 |
|  | pCIB171 | 72.5 ± 2.7 |
|  | pCIB176 | 75.0 ± 1.3 |
|  | pCIB190 | 73.8 ± 2.9 |
|  | pCIB193 | 76.2 ± 1.6 |
|  | pCIB196 | 77.0 ± 2.2 |

Table 1 shows that a *E. coli* cell's ability to convert lysine to cadaverine increased when a CBD was co-expressed with a lysine decarboxylase (pCIB171, pCIB176, pCIB190, pCIB193, pCIB196) compared to the negative control (pCIB111), where only a lysine decarboxylase was expressed.

Example 10: Production of Cadaverine from Free Cells of H. alvei Co-Overexpressing Genes that Encode a CBD and Lysine Decarboxylase H. alvei was transformed with pCIB111, pCIB171, pCIB176, pCIB190, pCIB193, or pCIB196. Three single colonies from each transformation were grown overnight at 37° C. in 4 mL of LB medium with kanamycin (50 µg/mL). The following day, 0.6 mL of each overnight culture was added to 0.4 mL of lysine-HCl and PLP to a final concentration of 160 g/L and 0.1 mM, respectively. Each mixture was incubated at 37° C. for 2 hours. Cadaverine production from each sample was quantified using NMR, and yield was calculated by dividing the molar amount of cadaverine produced by the molar amount of lysine added. The yield from each sample after 2 hours is presented in Table 2.

TABLE 2

Production of cadaverine by H. avlei strains overproducing a CBD and a lysine decarboxylase.

| Strain | Plasmid | Cadaverine Yield (%) |
|---|---|---|
| H. alvei | pCIB111 | 53.1 ± 5.2 |
|  | pCIB171 | 72.5 ± 1.9 |
|  | pCIB176 | 77.6 ± 3.3 |
|  | pCIB190 | 74.3 ± 4.7 |
|  | pCIB193 | 78.6 ± 1.5 |
|  | pCIB196 | 79.2 ± 2.8 |

Table 2 shows that a H. alvei cell's ability to convert lysine to cadaverine increased when a CBD was co-expressed with a lysine decarboxylase (pCIB171, pCIB176, pCIB190, pCIB193, pCIB196) compared to the negative control (pCIB111), where only a lysine decarboxylase was expressed.

Example 11: Production of Cadaverine from Free Cells of H. alvei Co-Overexpressing Genes that Encode a CBD and a Mutant Lysine Decarboxylase The lysine decarboxylase gene in the plasmid pCIB193 was mutated at to change the amino acid residue position 320 (SEQ ID NO:23) using the primers K320L-F and K320L-R. The amino acid at the $320^{th}$ residue position was mutated from a lysine to a leucine (SEQ ID NO:22) to create plasmid pCIB357.

H. avlei was transformed with pCIB111, pCIB193, or pCIB357. Three single colonies from each transformation were grown overnight at 37° C. in 4 mL of LB medium with kanamycin (50 µg/mL). The following day, 0.6 mL of each overnight culture was added to 0.4 mL of lysine-HCl and PLP to a final concentration of 160 g/L and 0.1 mM, respectively. Each mixture was incubated at 37° C. for 2 hours. Cadaverine production from each sample was quantified using NMR, and yield was calculated by dividing the molar amount of cadaverine produced by the molar amount of lysine added. The yield from each sample after 2 hours is presented in Table 3.

TABLE 3

Production of cadaverine by H. avlei strains overproducing a CBD and a lysine decarboxylase.

| Strain | Plasmid | Cadaverine Yield (%) |
|---|---|---|
| H. avlei | pCIB111 | 48.4 ± 2.8 |
|  | pCIB193 | 77.2 ± 1.2 |
|  | pCIB357 | 91.7 ± 3.7 |

Table 3 shows that a H. alvei cell's ability to convert lysine to cadaverine was further increased when the lysine decarboxylase was mutated at amino acid position 320 from a lysine to a leucine (pCIB357) compared to either control that expressed the wild-type lysine decarboxylase protein (pCIB111, pCIB193).

Example 12: Determining the Amount of Lysine Decarboxylase Protein Produced when a CBD is Co-Expressed with the Lysine Decarboxylase To determine whether the co-expression of a CBD with the lysine decarboxylase caused any changes in the amount of protein produced that would lead to the change in activity produced, overnight cultures of H. alvei harboring either pCIB111 or pCIB193 were lysed and analyzed using SDS-PAGE in order to determine how much of the total protein consisted of the lysine decarboxylase polypeptide. Cell lysis was performed using a combination of freeze thaw and lysozyme. Lysed samples were treated with DNAse in order to remove most of the DNA. The result of the SDS-PAGE is shown in FIG. 1.

The results demonstrated that the amount of lysine decarboxylase in the soluble phase actually decreased when a CBD was co-overexpressed (FIG. 1, lanes 193-1 and 193-2) compared to when a CBD was not co-expressed (FIG. 1, lane 111). There was, however, no significant difference in the amount of protein in the insoluble phase and the amount of background protein was the same in both the soluble and insoluble fractions. This observation demonstrates that the increase in lysine decarboxylase activity of a cell co-expressing a CBD was not a result of the CBD increasing the amount of soluble lysine decarboxylase inside the cell. Instead, there is some other mechanism by which co-expression of the CBD increases the cell's ability to convert lysine to cadaverine. Not to be bound by theory, one hypothesis is that insertion of the CBD into the membrane alters the membrane permeability of the cell, which affects the transport of lysine or cadaverine into or out of the cell.

Example 13: Production of Cadaverine from Immobilized H. alvei Co-Overexpressing Genes that Encode a CBD and Lysine Decarboxylase To determine the cell's ability to bind to a cellulose substrate with and without expressing a CBD, H. alvei transformed with either pCIB111 or pCIB193 were grown overnight at 37° C. in 10 mL of LB medium with kanamycin (50 µg/mL). The following day, 8 mL of overnight cultures were poured into separate Petri dishes containing Whatman No. 1 filter paper and submerging the filter paper. The submerged filter paper was allowed to incubate overnight at room temperature with shaking at 100 rpm. The following day, the filter papers with the adhered cells were transferred to clean Petri dishes and washed with 5 mL of PBST buffer (pH 7.4) at room temperature for 20 minutes with shaking at 100 rpm. After the unbound cells were washed off, the filter papers were transferred to new Petri dishes, and 5 mL of lysine-HCl and PLP were added to a final concentration of 100 g/L and 0.1 mM, respectively. The petri dishes were incubated at 37° C. for 6 hours and shaking at 100 rpm. Cadaverine production from each Petri dish was quantified using NMR, and yield was calculated by dividing the molar amount of cadaverine produced by the molar amount of lysine added. The yield from each sample after 6 hours is presented in Table 4.

TABLE 4

Production of cadaverine by immobilized *H. alvei* strains overproducing a CBD and a lysine decarboxylase.

| Strain | Plasmid | Cadaverine Yield (%) |
|---|---|---|
| *H. alvei* | pCIB111 | 8.5 ± 2.2 |
| | pCIB193 | 36.2 ± 1.9 |

Table 4 shows that *H. alvei* cells expressing a CBD (pCIB193) can bind better to a cellulose substrate compared to cells that do not express a CBD (pCIB111). In addition, the bound cells are still able to catalyze the conversion of lysine to cadaverine. The activity observed in the control that does not express a CBD is most likely from residual cells that were not removed from the filter paper during the wash step.

Table of plasmids used in Examples

| Host | Protein(s) Overexpressed | Plasmid |
|---|---|---|
| | CadA | pCIB71 |
| | CadA, Npt | pCIB111 |
| | Lpp-OmpA | pCIB129 |
| | Lpp-OmpA | pCIB143 |
| | Lpp-OmpA-XynA | pCIB147 |
| | Lpp-OmpA-CBH1 | pCIB150 |
| | Lpp-OmpA-CBH2 | pCIB151 |
| | Lpp-OmpA-CEX | pCIB158 |
| | Lpp-OmpA-CCBP | pCIB161 |
| | Lpp-OmpA-XynA, CadA, Npt | pCIB171 |
| | Lpp-OmpA-CBH1, CadA, Npt | pCIB193 |
| | Lpp-OmpA-CBH2, CadA, Npt | pCIB190 |
| | Lpp-OmpA-CEX, CadA, Npt | pCIB196 |
| | Lpp-OmpA-CCBP, CadA, Npt | pCIB176 |
| *E. coli* | Lpp-OmpA-XynA, CadA, Npt | pCIB171 |
| *E. coli* | Lpp-OmpA-CBH1, CadA, Npt | pCIB193 |
| *E. coli* | Lpp-OmpA-CBH2, CadA, Npt | pCIB190 |
| *E. coli* | Lpp-OmpA-CEX, CadA, Npt | pCIB196 |
| *E. coli* | Lpp-OmpA-CCBP, CadA, Npt | pCIB176 |
| *H. avlei* | Lpp-OmpA-XynA, CadA, Npt | pCIB171 |
| *H. avlei* | Lpp-OmpA-CBH1, CadA, Npt | pCIB193 |
| *H. avlei* | Lpp-OmpA-CBH2, CadA, Npt | pCIB190 |
| *H. avlei* | Lpp-OmpA-CEX, CadA, Npt | pCIB196 |
| *H. avlei* | Lpp-OmpA-CCBP, CadA, Npt | pCIB176 |

Table of primer sequences used in Examples.

| Name | Sequence (5'-3') |
|---|---|
| cadA-F1 | GGCGAGCTCACACAGGAAACAGACCATGAACGTTATTGCAATATTGAATCAC |
| cadA-R1 | GGCTCTAGACCACTTCCCTTGTACGAGC |
| npt-F1 | GGCAAGCTTAAGAGACAGGATGAGGATCG |
| npt-R1 | GGCCATATGTCAGAAGAACTCGTCAAGAAG |
| cadA-F2 | ATTTCACACAGGAAACAGCTATGAACGTTATTGCAATATTGAATCAC |
| cadA-R2 | AGCTGTTTCCTGTGTGAAAT |
| lpp-F1 | GGCGAGCTCATGAAAGCTACTAAACTGGTACTG |
| lpp-R1 | CTGATCGATTTTAGCGTTGC |
| lpp-ompA-F | GCAACGCTAAAATCGATCAGAACAACAATGGCCCGACC |
| ompA-R | GGCTCTAGAACGGGTAGCGATTTCAGGAG |
| lpp-F2 | ATTTCACACAGGAAACAGCTATGAAAGCTACTAAACTGGTACTG |
| lpp-R2 | AGCTGTTTCCTGTGTGAAAT |
| XynA-F | GGCTCTAGAGTCGACGCGACCTGCTCTTACAACAT |
| XynA-R | GGCGCATGCCTGCAGTTACTGCTGATTACCAGAGCTGC |
| CBH1-F | GGCTCTAGAGTCGACTCTGGTGGTAACCCGCCAGG |
| CBH1-R | GGCGCATGCCTGCAGTTACAGGCACTGAGAGTAGTACG |
| CBH2-F | GGCTCTAGAGTCGACGTTTGGGGTCAGTGCGGTGG |
| CBH2-R | GGCGCATGCCTGCAGTTAACCAACCGGCGGAACACGAG |
| CEX-F | GGCTCTAGAGTCGACGGTGCGTCTCCTACCCCAAC |
| CEX-R | GGCGCATGCCTGCAGTTAACCAACGGTGCACGGGGTAC |
| CCBP-F | GGCTCTAGAGTCGACACCACTCCAACCCCAACG |
| CCBP-R | GGCGCATGCCTGCAGTTACGTTACGGCAGACGCGGTCG |
| cadA-F3 | GGCTCTAGAATTTCACACAGGAAACAGCT |
| npt-F2 | CAAGGCGCGTATGCCCGACG |
| npt-R2 | CGTCGGGCATACGCGCCTTG |
| K320L-F | ACCGACTTCATCAAGCTGACACTGGATGTGAAATCCATC |
| K320L-R | GATTTCACATCCAGTGTCAGCTTGATGAAGTCGGTGTTG |

Illustrative Nucleic Acid and Polypeptide Sequences:

*Cellomonas fimi* exoglucanase polypeptide sequence-CBD sequence is underlined

SEQ ID NO: 1

MPRTTPAPGHPARGARTALRTTLAAAAATLVVGATVVLPAQAATTLKEAADGAGRDFGFALDPNRLSEAQYKAIADS

EFNLVVAENAMKWDATEPSQNSFSFGAGDRVASYAADTGKELYGHTLVWHSQLPDWAKNLNGSAFESAMVNHVTKVA

DHFEGKVASWDVVNEAFADGGGRRQDSAFQQKLGNGYIETAFRAARAADPTAKLCINDYNVEGINAKSNSLYDLVKD

FKARGVPLDCVGFQSHLIVGQVPGDFRQNLQRFADLGVDVRITELDIRMRTPSDATKLATQAADYKKVVQACMQVTR

-continued

CQGVTVWGITDKYSWVPDVFPGEGAALVWDASYAKKPAYAAVMEAFGASPTPTPTTPTPTPTTPTPTPT<u>SGPAGCQV</u>

<u>LWGVNQWNTGFTANVTVKNTSSAPVDGWTLTFSFPSGQQVTQAWSSTVTQSGSAVTVRNAPWNGSIPAGGTAQFGFN</u>

<u>GSHTGTNAAPTAFSLNGTPC</u>TVG

Codon optimized nucleotide sequence including the *Cellomonas fimi*
exoglucanase CBD

SEQ ID NO: 2

GGTGCGTCTCCTACCCCAACTCCAACCACCCCGACCCCGACCCCGACCACTCCGACGCCAACGCCGACCTCTGGTCC

AGCGGGTTGCCAGGTTCTGTGGGGTGTTAACCAGTGGAACACCGGCTTCACCGCGAACGTTACCGTGAAAAACACCT

CTTCTGCCCCGGTTGACGGTTGGACCCTGACCTTCTCTTTCCCGTCTGGTCAGCAGGTTACCCAGGCGTGGTCTTCT

ACCGTTACGCAGTCTGGTTCTGCGGTGACCGTTCGTAACGCGCCGTGGAATGGTTCCATCCCGGCTGGCGGTACGGC

CCAGTTCGGCTTTAACGGTTCCCACACCGGTACCAATGCGGCACCGACCGCGTTCTCTCTGAACGGTACCCCGTGCA

CCGTTGGT

*Cellomonas fimi* cellulose binding protein polypeptide sequence-CBD sequence
is underlined

SEQ ID NO: 3

MTTTLSRRLAGTLAALLLALAGALALAGPTQAADPVRIMPLGDSITGNPGCWRALLWQKLQQGGHTDVDMVGTLPAQ

GCGVAHDGNEGHGGYLVTDVAAQGQLVGWLAATDPDVVVMHFGTNDVWSARTTQQILDAYTTLVQQMRASNPQMRV

LVAQIIPVAPPTCAQCPARTAALNAAIPAWAAGITTAQSPVVVVDQATGWVPATDTSDGVHPDEDGIVKLADRWYPA

LAAVLDGTTPTPTPTPTVSPTPTPTPSVTPTPTPTPGGA<u>TCTASYAVSSQWQGGFVASVRVTATSPVSSWTVA</u>

<u>VTLPGGAVQHAWSATATTSGSTATFANAAWNGTLAAGQQADLGFQGTGSPTASAVT</u>CTATR

Codon optimized nucleotide sequence including the *Cellomonas fimi* cellulose
binding protein CBD

SEQ ID NO: 4

ACCACTCCAACCCCAACGCCGACTCCGACGCCTACCGTTAGCCCTACTCCTACCCCGACCCCTACGCCGTCTGTTAC

GCCAACTCCAACCCCAACGCCTGGTGGTGCGACCTGCACCGCATCTTACGCGGTTAGCTCTCAGTGGCAGGGCGGTT

TTGTTGCGAGCGTTCGTGTTACCGCCACCTCCCCGGTTTCTAGCTGGACCGTTGCGGTTACCCTGCCGGGTGGCGCG

GTTCAACATGCGTGGTCTGCGACGGCAACCACCTCTGGTTCTACCGCGACCTTTGCGAACGCGGCGTGGAACGGTAC

GCTGGCTGCTGGTCAGCAGGCGGACCTGGGCTTCCAGGGTACCGGCTCTCCGACCGCGTCTGCCGTAACG

*Clostridium thermocellum* CipA polypeptide sequence-CBD sequence is
underlined

SEQ ID NO: 5

MRKVISMLLVVAMLTTIFAAMIPQTVSAATMTVEIGKVTAAVGSKVEIPITLKGVPSKGMANCDFVLGYDPNVLEVT

EVKPGSIIKDPDPSKSFDSAIYPDRKMIVFLFAEDSGRGTYAITQDGVFATIVATVKSAAAAPITLLEVGAFADNDL

VEISTTFVAGGVNLGSSVPTTQPNVPSDGVVVEIGKVTGSVGTTVEIPVYFRGVPSKGIANCDFVFRYDPNVLEIIG

IDPGDIIVDPNPTKSFDTAIYPDRKIIVFLFAEDSGTGAYAITKDGVFAKIRATVKSSAPGYITFDEVGGFADNDLV

EQKVSFIDGGVNVGNATPTKGATPTNTATPTKSATATPTRPSVPTNTPTNTPANTPVSGNLK<u>VEFYNSNPSDTTNSI</u>

<u>NPQFKVTNTGSSAIDLSKLTLRYYYTVDGQKDQTFWCDHAAIIGSNGSYNGITSNVKGTFVKMSSSTNNADTYLEIS</u>

FTGGTLEPGAHVQIQGRFAKNDWSNYTQSNDYSFKSASQFVEWDQVTAYLNGVLVWGKEPGGSVVPSTQPVTTPPAT

TKPPATTKPPATTIPPSDDPNAIKIKVDTVNAKPGDTVNIPVRFSGIPSKGIANCDFVYSYDPNVLEIIEIKPGELI

VDPNPDKSFDTAVYPDRKIIVFLFAEDSGTGAYAITKDGVFATIVAKVKSGAPNGLSVIKFVEVGGFANNDLVEQRT

QFFDGGVNVGDTTVPTTPTTPVTTPTDDSNAVRIKVDTVNAKPGDTVRIPVRFSGIPSKGIANCDFVYSYDPNVLEI

IEIEPGDIIVDPNPDKSFDTAVYPDRKIIVFLFAEDSGTGAYAITKDGVFATIVAKVKSGAPNGLSVIKFVEVGGFA

NNDLVEQKTQFFDGGVNVGDTTEPATPTTPVTTPTTTDDLDAVRIKVDTVNAKPGDTVRIPVRFSGIPSKGIANCDF

VYSYDPNVLEIIEIEPGDIIVDPNPDKSFDTAVYPDRKIIVFLFAEDSGTGAYAITKDGVFATIVAKVKSGAPNGLS

VIKFVEVGGFANNDLVEQKTQFFDGGVNVGDTTEPATPTTPVTTPTTTDDLDAVRIKVDTVNAKPGDTVRIPVRFSG

IPSKGIANCDFVYSYDPNVLEIIEIEPGDIIVDPNPDKSFDTAVYPDRKIIVFLFAEDSGTGAYAITKDGVFATIVA

KVKEGAPNGLSVIKFVEVGGFANNDLVEQKTQFFDGGVNVGDTTEPATPTTPVTTPTTTDDLDAVRIKVDTVNAKPG

-continued

```
DTVRIPVRFSGIPSKGIANCDFVYSYDPNVLEIIEIEPGELIVDPNPTKSFDTAVYPDRKMIVFLFAEDSGTGAYAI

TEDGVFATIVAKVKSGAPNGLSVIKFVEVGGFANNDLVEQKTQFFDGGVNVGDTTEPATPTTPVTTPTTTDDLDAVR

IKVDTVNAKPGDTVRIPVRFSGIPSKGIANCDFVYSYDPNVLEIIEIEPGDIIVDPNPDKSFDTAVYPDRKIIVFLF

AEDSGTGAYAITKDGVFATIVAKVKEGAPNGLSVIKFVEVGGFANNDLVEQKTQFFDGGVNVGDTTVPTTSPTTTPP

EPTITPNKLTLKIGRAEGRPGDTVEIPVNLYGVPQKGIASGDFVVSYDPNVLEIIEIEPGELIVDPNPTKSFDTAVY

PDRKMIVFLFAEDSGTGAYAITEDGVFATIVAKVKEGAPEGFSAIEISEFGAFADNDLVEVETDLINGGVLVTNKPV

IEGYKVSGYILPDFSFDATVAPLVKAGFKVEIVGTELYAVTDANGYFEITGVPANASGYTLKISRATYLDRVIANVV

VTGDTSVSTSQAPIMMWVGDIVKDNSINLLDVAEVIRCFNATKGSANYVEELDINRNGAINMQDIMIVHKHFGATSS

DYDAQ
```

Clostridium thermocellum partial CipB polypeptide sequence-CBD sequence is underlined
SEQ ID NO: 6
```
DPSKSFDSAIYPDRKMIVFLFAEDSGRGTYAITQDGVFATIVATVKSAAAAPITLLEVGAFRDNDLVEISTTFVAGG

VNLGSSVPTTQPNVPSDGVVVEIGKVTGSVGTTVEIPVYFRGVPSKGIANCDFVFRYDPNVLEIIGIDPRSIIVDPN

PTKSFDTAIYADRKIIVFLFCGRQRNRSVSITKDGVFAKIRATVKSSAPAYITFDEVGGFADNDLVEQKVSFIDGGV

NVGNATPTKGATPTNTATPTKSATATPPGHSVPTNTPTNPANTPVSGNLKVEFYNSNPSDTTNSINPQFKVTNTGS

SAIDLSKLTLRYYYTVDGQKDQTFWCDHAAIIGSNGSYNGITSNVKGTFVKMSSSTNNADTYLEISFTGGTLEPGAH

VQIQGRFAKNDWSNYTQSNDYSFKSRSQFVEWDQVTAYLNGVLVWGKEPGGSVVPSTQPVTTPPATTKPPATTIPPS

DDPNAIKIKVDTVNAKPGDTVNIPVRFSGIPSKGIANCDFVYSYDPNVLEIIEIKPGELIVDPNPDKSFDTAVYPDR

KMIVFLFAEDSGTGAYAITEDGVFATIVAKVKEGAPEGFSAIEISEFGAFADNDLVEVETDLINGGVLVTNKPVIEG

YKVSGYILPDFSFDATVAPLVKAGFKVEIVGTELYAVTDANGYFEITGVPANASGYTLKISRATYLDRVIANVVVTG

DTSVSTSQAPIMMWVGDIVKDNSINLLDVAEVIRCFNATKGSANYVEELDINRNGAINMQDIMIVHKHFGATSSDYD

AQ
```

Trichoderma reesei cellobiohydrylase I polypeptide sequence-CBD sequence is underlined
SEQ ID NO: 7
```
MYRKLAVISAFLATARAQSACTLQSETHPPLTWQKCSSGGTCTQQTGSVVIDANWRWTHATNSSTNCYDGNTWSSTL

CPDNETCAKNCCLDGAAYASTYGVTTSGNSLSIGFVTQSAQKNVGARLYLMASDTTYQEFTLLGNEFSFDVDVSQLP

CGLNGALYFVSMDADGGVSKYPTNTAGAKYGTGYCDSQCPRDLKFINGQANVEGWEPSSNNANTGIGGHGSCCSEMD

IWEANSISEALTPHPCTTVGQEICEGDGCGGTYSDNRYGGTCDPDGCDWNPYRLGNTSFYGPGSSFTLDTTKKLTVV

TQFETSGAINRYYVQNGVTFQQPNAELGSYSGNELNDDYCTAEEAEFGGSSFSDKGGLTQFKKATSGGMVLVMSLWD

DYYANMLWLDSTYPTNETSSTPGAVRGSCSTSSGVPAQVESQSPNAKVTFSNIKFGPIGSTGNPSGGNPPGGNRGTT

TTRRPATTTGSSPGPTQSHYGQCGGIGYSGPTVCASGTTCQVLNPYYSQCL
```

Codon optimized nucleotide sequence including the Trichoderma reesei cellobiohydrylase I CBD
SEQ ID NO: 8
```
TCTGGTGGTAACCCGCCAGGTGGCAACCGTGGCACCACCACTACGCGTCGTCCGGCGACTACGACCGGTTCTTCTCC

GGGTCCGACGCAGTCTCACTACGGTCAGTGCGGTGGTATCGGTTACTCTGGCCCGACCGTTTGCGCGTCTGGTACGA

CCTGCCAGGTTCTGAACCCGTACTACTCTCAGTGCCTG
```

Trichoderma reesei cellobiohydrylase II polypeptide sequence-CBD sequence is underlined
SEQ ID NO: 9
```
MIVGILTTLATLATLAASVPLEERQACSSVWGQCGGQNWSGPTCCASGSTCVYSNDYYSQCLPGAASSSSTRAAST

TSRVSPTTSRSSSATPPPGSTTTRVPPVGSGTATYSGNPFVGVTPWANAYYASEVSSLAIPSLTGAMATAAAAVAKV

PSFMWLDTLDKTPLMEQTLADIRTANKNGGNYAGQFVVYDLPDRDCAALASNGEYSIADGGVAKYKNYIDTIRQIVV

EYSDIRTLLVIEPDSLANLVTNLGTPKCANAQSAYLECINYAVTQLNLPNVAMYLDAGHAGWLGWPANQDPAAQLFA
```

-continued

NVYKNASSPRALRGLATNVANYNGWNITSPPSYTQGNAVYNEKLYIHAIGPLLANHGWSNAFFITDQGRSGKQPTGQ

QQWGDWCNVIGTGFGIRPSANTGDSLLDSFVWVKPGGECDGTSDSSAPRFDSHCALPDALQPAPQAGAWFQAYFVQL

LTNANPSFL

Codon optimized nucleotide sequence including the *Trichoderma reesei*
cellobiohydrylase II CBD

SEQ ID NO: 10

GTTTGGGGTCAGTGCGGTGGTCAGAACTGGTCTGGTCCGACCTGCTGCGCGTCTGGTTCTACCTGCGTTTACTCTAA

CGACTACTACTCTCAGTGCCTGCCGGGTGCTGCGTCTTCTAGCTCTTCTACCCGTGCGGCGTCTACCACCTCTCGTG

TGTCTCCGACTACCTCCCGTTCTTCTTCTGCGACCCCACCGCCAGGCTCTACTACCACTCGTGTTCCGCCGGTTGGT

*Cellvibrio japonicas* XynA polypeptide sequence-CBD sequence is underlined

SEQ ID NO: 11

MRTAMAKSLGAAAFLGAALFAHTLAAQTATCSYNITNEWNTGYTGDITITNRGSSAINGWSVNWQYATNRLSSSWNA

NVSGSNPYSASNLSWNGNIQPGQSVSFGFQVNKNGGSAERPSVGGSICSGSVASSSAPASSVPSSIASSSPSSVASS

VISSMASSSPVSSSSVASSTPGSSSGNQQCNWYGTLYPLCVTTTNGWGWEDQRSCIARSTCAAQPAPFGIVGSGSST

PVSSSSSLSSSSVVSSIRSSSSSSSSSVATGNGLASLADFPIGVAVAASGGNADIFTSSARQNIVRAEFNQITAEN

IMKMSYMYSGSNFSFTNSDRLVSWAAQNGQTVHGHALVWHPSYQLPNWASDSNANFRQDFARHIDTVAAHFAGQVKS

WDVVNEALFDSADDPDGRGSANGYRQSVFYRQFGGPEYIDEAFRRARAADPTAELYYNDFNTEENGAKTTALVNLVQ

RLLNNGVPIDGVGFQMHVMNDYPSIANIRQAMQKIVALSPTLKIKITELDVRLNNPYDGNSSNDYTNRNDCAVSCAG

LDRQKARYKEIVQAYLEVVPPGRRGGITVWGIADPDSWLYTHQNLPDWPLLFNDNLQPKPAYQGVVEALSGR

Codon optimized nucleotide sequence including the *Cellvibrio japonicas* XynA
CBD

SEQ ID NO: 12

GCGACCTGCTCTTACAACATCACCAACGAATGGAACACCGGTTACACCGGCGACATTACCATCACTAATCGTGGTTC

TTCTGCGATCAACGGTTGGTCTGTTAACTGGCAATATGCTACGAACCGCCTGTCTTCTAGCTGGAACGCGAACGTTT

CTGGTTCTAACCCGTACTCTGCGTCTAACCTCTCTTGGAACGGTAACATCCAGCCGGGTCAGTCTGTTTCCTTTGGT

TTCCAGGTTAACAAAAACGGCGGCTCTGCTGAGCGTCCGTCTGTTGGTGGTAGCATCTGCTCTGGCTCTGTTGCGTC

CTCTTCCGCGCCAGCTTCTTCCGTCCCATCTTCTATCGCGTCTTCTTCTCCGTCTAGCGTTGCCTCCAGCGTTATCT

CTTCCATGGCGTCCAGCTCTCCGGTTAGCTCCAGCAGCGTAGCGAGCAGCACCCCGGGTAGCAGCTCTGGTAATCAG

CAG

*Cellomonas fimi* exoglucanase CBD amino acid sequence

SEQ ID NO: 13

SGPAGCQVLWGVNQWNTGFTANVTVKNTSSAPVDGWTLTFSFPSGQQVTQAWSSTVTQSGSAVTVRNAPWNGSIPAG

GTAQFGFNGSHTGTNAAPTAFSLNGTPC

*Cellomonas fimi* cellulose binding protein CBD amino acid sequence

SEQ ID NO: 14

TCTASYAVSSQWQGGFVASVRVTATSPVSSWTVAVTLPGGAVQHAWSATATTSGSTATFANAAWNGTLAAGQQADLG
FQGTGSPTASAVT

*Clostridium thermocellum* CipA CBD amino acid sequence

SEQ ID NO: 15

VEFYNSNPSDTTNSINPQFKVTNTGSSAIDLSKLTLRYYYTVDGQKDQTFWCDHAAIIGSNGSYNGITSNVKGTFVK

MSSSTNNADTYLEIS

*Clostridium thermocellum* Cip B CBD amino acid sequence

SEQ ID NO: 16

VEFYNSNPSDTTNSINPQFKVTNTGSSAIDLSKLTLRYYYTVDGQKDQTFWCDHAAIIGSNGSYNGITSNVKGTFVK

MSSSTNNADTYLEIS

*Trichoderma reesei* cellobiohydrylase I CBD sequence amino acid sequence

SEQ ID NO: 17

HYGQCGGIGYSGPTVCASGTTCQVLNPYYSQ

*Trichoderma reesei* cellobiohydrylase II CBD amino acid sequence

SEQ ID NO: 18

VWGQCGGQNWSGPTCCASGSTCVYSNDYYS

Cellvibrio japonicas XynA CBD amino acid sequence

SEQ ID NO: 19

ATCSYNITNEWNTGYTGDITITNRGSSAINGWSVNWQYATNR

CadA polypeptide sequence

SEQ ID NO: 20

MNVIAILNHMGVYFKEEPIRELHRALERLNFQIVYPNDRDDLLKLIENNARLCGVIFDWDKYNLELCEEISKMNENL

PLYAFANTYSTLDVSLNDLRLQISFFEYALGAAEDIANKIKQTTDEYINTILPPLTKALFKYVREGKYTFCTPGHMG

GTAFQKSPVGSLFYDFFGPNTMKSDISISVSELGSLLDHSGPHKEAEQYIARVFNADRSYMVTNGTSTANKIVGMYS

APAGSTILIDRNCHKSLTHLMMMSDVTPIYFRPTRNAYGILGGIPQSEFQHATIAKRVKETPNATWPVHAVITNSTY

DGLLYNTDFIKKTLDVKSIHFDSAWVPYTNFSPIYEGKCGMSGGRVEGKVIYETQSTHKLLAAFSQASMIHVKGDVN

EETFNEAYMMEITTTSPHYGIVASTETAAAMMKGNAGKRLINGSIERAIKFRKEIKRLRTESDGWFFDVWQPDHIDT

TECWPLRSDSTWHGFKNIDNEHMYLDPIKVTLLTPGMEKDGTMSDFGIPASIVAKYLDEHGIVVEKTGPYNLLFLFS

IGIDKTKALSLLRALTDFKRAFDLNLRVKNMLPSLYREDPEFYENIVIRIQELAQNIHKLIVEIHNLPDLMYRAFEV

LPTMVMTPYAAFQKELHGMTEEVYLDEMVGRINANMILPYPPGVPLVMPGEMITEESRPVLEFLQMLCEIGAHYPGF

ETDIRGAYRQADGRYTVKVLKEESKK

Escherichia coli cadA nucleic acid sequence

SEQ ID NO: 21

ATGAACGTTATTGCAATATTGAATCACATGGGGGTTTATTTTAAAGAAGAACCCATCCGTGAACTTCATCGCGCGCT

TGAACGTCTGAACTTCCAGATTGTTTACCCGAACGACCGTGACGACTTATTAAAACTGATCGAAAACAATGCGCGTC

TGTGCGGCGTTATTTTTGACTGGGATAAATATAATCTCGAGCTGTGCGAAGAAATTAGCAAAATGAACGAGAACCTG

CCGTTGTACGCGTTCGCTAATACGTATTCCACTCTCGATGTAAGCCTGAATGACCTGCGTTTACAGATTAGCTTCTT

TGAATATGCGCTGGGTGCTGCTGAAGATATTGCTAATAAGATCAAGCAGACCACTGACGAATATATCAACACTATTC

TGCCTCCGCTGACTAAAGCACTGTTTAAATATGTTCGTGAAGGTAAATATACTTTCTGTACTCCTGGTCACATGGGC

GGTACTGCATTCCAGAAAAGCCCGGTAGGTAGCCTGTTCTATGATTTCTTTGGTCCGAATACCATGAAATCTGATAT

TTCCATTTCAGTATCTGAACTGGGTTCTCTGCTGGATCACAGTGGTCCACACAAAGAAGCAGAACAGTATATCGCTC

GCGTCTTTAACGCAGACCGCAGCTACATGGTGACCAACGGTACTTCCACTGCGAACAAAATTGTTGGTATGTACTCT

GCTCCAGCAGGCAGCACCATTCTGATTGACCGTAACTGCCACAAATCGCTGACCCACCTGATGATGATGAGCGATGT

TACGCCAATCTATTTCCGCCCGACCCGTAACGCTTACGGTATTCTTGGTGGTATCCCACAGAGTGAATTCCAGCACG

CTACCATTGCTAAGCGCGTGAAAGAAACACCAAACGCAACCTGGCCGGTACATGCTGTAATTACCAACTCTACCTAT

GATGGTCTGCTGTACAACACCGACTTCATCAAGAAAACACTGGATGTGAAATCCATCCACTTTGACTCCGCGTGGGT

GCCTTACACCAACTTCTCACCGATTTACGAAGGTAAATGCGGTATGAGCGGTGGCCGTGTAGAAGGGAAAGTGATTT

ACGAAACCCAGTCCACTCACAAACTGCTGGCGGCGTTCTCTCAGGCTTCCATGATCCACGTTAAAGGTGACGTAAAC

GAAGAAACCTTTAACGAAGCCTACATGATGCACACCACCACTTCTCCGCACTACGGTATCGTGGCGTCCACTGAAAC

CGCTGCGGCGATGATGAAAGGCAATGCAGGTAAGCGTCTGATCAACGGTTCTATTGAACGTGCGATCAAATTCCGTA

AAGAGATCAAACGTCTGAGAACGGAATCTGATGGCTGGTTCTTTGATGTATGGCAGCCGGATCATATCGATACGACT

GAATGCTGGCCGCTGCGTTCTGACAGCACCTGGCACGGCTTCAAAAACATCGATAACGAGCACATGTATCTTGACCC

GATCAAAGTCACCCTGCTGACTCCGGGGATGGAAAAAGACGGCACCATGAGCGACTTTGGTATTCCGGCCAGCATCG

TGGCGAAATACCTCGACGAACATGGCATCGTTGTTGAGAAAACCGGTCCGTATAACCTGCTGTTCCTGTTCAGCATC

GGTATCGATAAGACCAAAGCACTGAGCCTGCTGCGTGCTCTGACTGACTTTAAACGTGCGTTCGACCTGAACCTGCG

TGTGAAAAACATGCTGCCGTCTCTGTATCGTGAAGATCCTGAATTCTATGAAAACATGCGTATTCAGGAACTGGCTC

AGAATATCCACAAACTGATTGTTCACCACAATCTGCCGGATCTGATGTATCGCGCATTTGAAGTGCTGCCGACGATG

GTAATGACTCCGTATGCTGCATTCCAGAAAGAGCTGCACGGTATGACCGAAGAAGTTTACCTCGACGAAATGGTAGG

-continued

```
TCGTATTAACGCCAATATGATCCTTCCGTACCCGCCGGGAGTTCCTCTGGTAATGCCGGGTGAAATGATCACCGAAG
AAAGCCGTCCGGTTCTGGAGTTCCTGCAGATGCTGTGTGAAATCGGCGCTCACTATCCGGGCTTTGAAACCGATATT
CACGGTGCATACCGTCAGGCTGATGGCCGCTATACCGTTAAGGTATTGAAAGAAGAAAGCAAAAAATAA
```

CadA mutant K320L polypeptide sequence-mutation underlined

SEQ ID NO: 22

```
MNVIAILNHMGVYFKEEPIRELHRALERLNFQIVYPNDRDDLLKLIENNARLCGVIEDWDKYNLELCEEISKMNENL
PLYAFANTYSTLDVSLNDLRLQISFFEYALGAAEDIANKIKQTTDEYINTILPPLTKALFKYVREGKYTFCTPGHMG
GTAFQKSPVGSLFYDFFGPNTMKSDISISVSELGSLLDHSGPHKEAEQYIARVFNADRSYMVTNGTSTANKIVGMYS
APAGSTILIDRNCHKSLTHLMMMSDVTPIYFRPTRNAYGILGGIPQSEFQHATIAKRVKETPNATWPVHAVITNSTY
DGLLYNTDFIKLTLDVKSIHEDSAWVPYTNESPIYEGKCGMSGGRVEGKVIYETQSTHKLLAAFSQASMIHVKGDVN
EETFNEAYMMHTTTSPHYGIVASTETAAAMMKGNAGKRLINGSIERAIKFRKEIKRLRTESDGWFFDVWQPDHIDTT
ECWPLRSDSTWHGFKNIDNEHMYLDPIKVTLLTPGMEKDGTMSDFGIPASIVAKYLDEHGIVVEKTGPYNLLFLFSI
GIDKTKALSLLRALTDFKRAFDLNLRVKNMLPSLYREDPEFYENMRIQELAQNIHKLIVHHNLPDLMYRAFEVLPTM
VMTPYAAFQKELHGMTEEVYLDEMVGRINANMILPYPPGVPLVMPGEMITEESRPVLEFLQMLCEIGAHYPGFETDI
HGAYRQADGRYTVKVLKEESKK
```

*Escherichia coli* cadA mutant K320L nucleic acid sequence-mutation underlined

SEQ ID NO: 23

```
ATGAACGTTATTGCAATATTGAATCACATGGGGGTTTATTTTAAAGAAGAACCCATCCGTGAACTTCATCGCGCGCT
TGAACGTCTGAACTTCCAGATTGTTTACCCGAACGACCGTGACGACTTATTAAAACTGATCGAAAACAATGCGCGTC
TGTGCGGCGTTATTTTTGACTGGGATAAATATAATCTCGAGCTGTGCGAAGAAATTAGCAAAATGAACGAGAACCTG
CCGTTGTACGCGTTCGCTAATACGTATTCCACTCTCGATGTAAGCCTGAATGACCTGCGTTTACAGATTAGCTTCTT
TGAATATGCGCTGGGTGCTGCTGAAGATATTGCTAATAAGATCAAGCAGACCACTGACGAATATATCAACACTATTC
TGCCTCCGCTGACTAAAGCACTGTTTAAATATGTTCGTGAAGGTAAATATACTTTCTGTACTCCTGGTCACATGGGC
GGTACTGCATTCCAGAAAAGCCCGGTAGGTAGCCTGTTCTATGATTTCTTTGGTCCGAATACCATGAAATCTGATAT
TTCCATTTCAGTATCTGAACTGGGTTCTCTGCTGGATCACAGTGGTCCACACAAAGAAGCAGAACAGTATATCGCTC
GCGTCTTTAACGCAGACCGCAGCTACATGGTGACCAACGGTACTTCCACTGCGAACAAAATTGTTGGTATGTACTCT
GCTCCAGCAGGCAGCACCATTCTGATTGACCGTAACTGCCACAAATCGCTGACCCACCTGATGATGATGAGCGATGT
TACGCCAATCTATTTCCGCCCGACCCGTAACGCTTACGGTATTCTTGGTGGTATCCCACAGAGTGAATTCCAGCACG
CTACCATTGCTAAGCGCGTGAAAGAAACACCAAACGCAACCTGGCCGGTACATGCTGTAATTACCAACTCTACCTAT
GATGGTCTGCTGTACAACACCGACTTCATCAAGCTGACACTGGATGTGAAATCCATCCACTTTGACTCCGCGTGGGT
GCCTTACACCAACTTCTCACCGATTTACGAAGGTAAATGCGGTATGAGCGGTGGCCGTGTAGAAGGGAAAGTGATTT
ACGAAACCCAGTCCACTCACAAACTGCTGGCGGCGTTCTCTCAGGCTTCCATGATCCACGTTAAAGGTGACGTAAAC
GAAGAAACCTTTAACGAAGCCTACATGATGCACACCACCACTTCTCCGCACTACGGTATCGTGGCGTCCACTGAAAC
CGCTGCGGCGATGATGAAAGGCAATGCAGGTAAGCGTCTGATCAACGGTTCTATTGAACGTGCGATCAAATTCCGTA
AAGAGATCAAACGTCTGAGAACGGAATCTGATGGCTGGTTCTTTGATGTATGGCAGCCGGATCATATCGATACGACT
GAATGCTGGCCGCTGCGTTCTGACAGCACCTGGCACGGCTTCAAAAACATCGATAACGAGCACATGTATCTTGACCC
GATCAAAGTCACCCTGCTGACTCCGGGGATGGAAAAAGACGGCACCATGAGCGACTTTGGTATTCCGGCCAGCATCG
TGGCGAAATACCTCGACGAACATGGCATCGTTGTTGAGAAAACCGGTCCGTATAACCTGCTGTTCCTGTTCAGCATC
GGTATCGATAAGACCAAAGCACTGAGCCTGCTGCGTGCTCTGACTGACTTTAAACGTGCGTTCGACCTGAACCTGCG
TGTGAAAAACATGCTGCCGTCTCTGTATCGTGAAGATCCTGAATTCTATGAAAACATGCGTATTCAGGAACTGGCTC
AGAATATCCACAAACTGATTGTTCACCACAATCTGCCGGATCTGATGTATCGCGCATTTGAAGTGCTGCCGACGATG
GTAATGACTCCGTATGCTGCATTCCAGAAAGAGCTGCACGGTATGACCGAAGAAGTTTACCTCGACGAAATGGTAGG
TCGTATTAACGCCAATATGATCCTTCCGTACCCGCCGGGAGTTCCTCTGGTAATGCCGGGTGAAATGATCACCGAAG
```

```
AAAGCCGTCCGGTTCTGGAGTTCCTGCAGATGCTGTGTGAAATCGGCGCTCACTATCCGGGCTTTGAAACCGATATT
CACGGTGCATACCGTCAGGCTGATGGCCGCTATACCGTTAAGGTATTGAAAGAAGAAAGCAAAAAATAA
```

*Escherichia coli* OmpA polypeptide sequence-the region used for surface display is underlined.

SEQ ID NO: 24

MKKTAIAIAVALAGFATVAQAAPKDNTWYTGAKLGWSQYHDTGFINNNGPTHENQLGAGAFGGYQVNPYVGFEMGYD

WLGRMPYKGSVENGAYKAQGVQLTAKLGYPITDDLDIYTRLGGMVWRADTKSNVYGKNHDTGVSPVFAGGVEYAITP

EIATRLEYQWTNNIGDAHTIGTRPDNGMLSLGVSYRFGQGEAAPVVAPAPAPAPEVQTKHFTLKSDVLFNFNKATLK

PEGQAALDQLYSQLSNLDPKDGSVVVLGYTDRIGSDAYNQGLSERRAQSVVDYLISKGIPADKISARGMGESNPVTG

NTCDNVKQRAALIDCLAPDRRVEIEVKGIKDVVTQPQA

Fusion polypeptide amino acid sequence containing the CBH1 CBD fused to the surface display region of OmpA encoded by a polynucleotide encoding a fusion protein comprising: E. coli lipoprotein leader sequence (italic) joined to an OmpA display region (underlined) joined to a CBH1 CBD (bold). The protein encoded by the The OmpA region is underlined.

SEQ ID NO: 25

*MKATKLVLGAVILGSTLLAGCSSNAKIDQ*NNNGPTHENQLGAGAFGGYQVNPYVGFEMGYDWLGRMPYKGSVENGAY

KAQGVQLTAKLGYPITDDLDIYTRLGGMVWRADTKSNVYGKNHDTGVSPVFAGGVEYAITPEIATRSRVDSGGNPPG

GNRGTTTTRRPATTTGSSPGPTQSHYGQCGGIGYSGPTVCASGTTCQVLNPYYSQC

---

What is claimed is:

1. A product, which is one of the following products I) to II):
   (I) A host cell genetically modified to (i) express a polynucleotide that encodes a carbohydrate binding module (CBM) fusion polypeptide on the cell surface and (ii) overexpress a lysine decarboxylase, wherein the CBM fusion polypeptide comprises a CBM joined to a surface display polypeptide and the polynucleotide that encodes the CBM fusion polypeptide comprises a region that encodes a leader peptide that is heterologous to the surface display polypeptide, wherein
   the CBM is a cellulose binding domain (CBD) from an exoglucanase, an endoglucanase, a cellulose binding protein, a cellobiohydrolase I, a cellobiohydrolase II, a xylanase, or a CipA or CipB inclusion protein;
   the leader peptide is an *Escherichia coli* lipoprotein (Lpp) leader peptide; and
   the surface display polypeptide comprises a region of OmpA,
   wherein the CBM is a CBD comprising the amino acid sequence of any one of SEQ ID NOS: 13-19, and the surface display polypeptide consists of amino acids 46-159 of SEQ ID NO: 24; and
   (II) a cell culture comprising a host cell of the product (I).

2. A product of claim 1, which is I) the host cell, wherein the lysine decarboxylase is:
   (a) an exogenous lysine decarboxylase expressed by a polynucleotide encoding the exogenous lysine decarboxylase that is introduced into the host cell; and/or
   (b) CadA; and/or
   (c) LdcC.

3. A product of claim 1, which is I) the host cell, wherein the CBM is
   at the C-terminal end of the fusion polypeptide or within 15 amino acids of the C-terminal end of the fusion polypeptide.

4. A product of claim 1, which is I) the host cell, wherein the host cell:
   (a) is from the genus *Escherichia*, *Hafnia*, or Corynebacteria; or
   (b) is an *Escherichia coli*, *Hafnia alvei*, or *Corynebacterium glutamicum* cell.

5. A product of claim 1, which is II) the cell culture, wherein the cell culture is incubated with a carbohydrate substrate.

6. A product of claim 5, wherein the carbohydrate substrate is a cellulose substrate.

7. A method, which is one of the following methods I) to II):
   (I) a method of producing cadaverine, the method comprising
      incubating a cell culture comprising a host cell with a carbohydrate substrate, wherein the host cell is genetically modified to express a polynucleotide that encodes a carbohydrate binding module (CBM) fusion polypeptide on the cell surface and to overexpress lysine decarboxylase under condition in which the CBM fusion polypeptide and the lysine decarboxylase are expressed, wherein the CBM fusion polypeptide comprises a CBM joined to a surface display polypeptide and the polynucleotide that encodes the CBM fusion polypeptide comprises a region that encodes a leader peptide that is heterologous to the surface display polypeptide, wherein
      the CBM is a cellulose binding domain (CBD) from an exoglucanase, an endoglucanase, a cellulose binding protein, a cellobiohydrolase I, a cellobiohydrolase II, a xylanase, or a CipA or CipB inclusion protein;
      the leader peptide is an *Escherichia coli* lipoprotein (Lpp) leader peptide; and
      the surface display polypeptide comprises a region of OmpA,
      wherein the CBM is a CBD comprising the amino acid sequence of any one of SEQ ID NOS: 13-19, and the surface display polypeptide consists of amino acids 46-159 of SEQ ID NO: 24; and (II) a method of obtaining a genetically modified host cell for the production of cadaverine, the method comprising:

expressing a polynucleotide that encodes a carbohydrate binding module (CBM) fusion polypeptide on the cell surface in a host cell genetically modified to overexpress a lysine decarboxylase, wherein the CBM fusion polypeptide comprises a CBM joined to a surface display polypeptide and the polynucleotide that encodes the CBM fusion polypeptide comprises a region that encodes a leader peptide that is heterologous to the surface display polypeptide, wherein the CBM is a cellulose binding domain (CBD) from an exoglucanase, an endoglucanase, a cellulose binding protein, a cellobiohydrolase I, a cellobiohydrolase II, a xylanase, or a CipA or CipB inclusion protein;

the leader peptide is an *Escherichia coli* lipoprotein (Lpp) leader peptide; and the surface display polypeptide comprises a region of OmpA; and selecting a host cell that produces an increased amount of cadaverine compared to a counterpart host cell that does not overexpress the lysine decarboxylase, wherein the CBM is a CBD comprising the amino acid sequence of any one of SEQ ID NOS: 13-19, and the surface display polypeptide consists of amino acids 46-159 of SEQ ID NO: 24.

8. The method of claim 7, wherein the lysine decarboxylase is:
(a) an exogenous lysine decarboxylase expressed by a polynucleotide encoding the exogenous lysine decarboxylase that is introduced into the host cell; and/or
(b) CadA; and/or
(c) LdcC.

9. The method of claim 7, wherein the CBM is
at the C-terminal end of the fusion polypeptide or within 15 amino acids of the C-terminal end of the fusion polypeptide.

10. The method of claim 7, wherein the carbohydrate substrate is a cellulose substrate.

11. The method of claim 7, wherein the host cell:
(a) is from the genus *Escherichia, Hafnia*, or Corynebacteria; or
(b) is an *Escherichia coli, Hafnia alvei*, or *Corynebacterium glutamicum* cell.

12. The method of claim 7, which is I) the method, further comprising isolating cadaverine.

\* \* \* \* \*

SEQUENCE LISTING

<160> NUMBER OF SEQ ID NOS: 52

<210> SEQ ID NO 1
<211> LENGTH: 485
<212> TYPE: PRT
<213> ORGANISM: Cellomonas fimi

<400> SEQUENCE: 1

Met Pro Arg Thr Thr Pro Ala Pro Gly His Pro Ala Arg Gly Ala Arg
1               5                   10                  15

Thr Ala Leu Arg Thr Leu Ala Ala Ala Ala Thr Leu Val Val
            20                  25                  30

Gly Ala Thr Val Val Leu Pro Ala Gln Ala Ala Thr Thr Leu Lys Glu
        35                  40                  45

Ala Ala Asp Gly Ala Gly Arg Asp Phe Gly Phe Ala Leu Asp Pro Asn
    50                  55                  60

Arg Leu Ser Glu Ala Gln Tyr Lys Ala Ile Ala Asp Ser Glu Phe Asn
65                  70                  75                  80

Leu Val Val Ala Glu Asn Ala Met Lys Trp Asp Ala Thr Glu Pro Ser
                85                  90                  95

Gln Asn Ser Phe Ser Phe Gly Ala Gly Asp Arg Val Ala Ser Tyr Ala
            100                 105                 110

Ala Asp Thr Gly Lys Glu Leu Tyr Gly His Thr Leu Val Trp His Ser
        115                 120                 125

Gln Leu Pro Asp Trp Ala Lys Asn Leu Asn Gly Ser Ala Phe Glu Ser
    130                 135                 140

Ala Met Val Asn His Val Thr Lys Val Ala Asp His Phe Glu Gly Lys
145                 150                 155                 160

Val Ala Ser Trp Asp Val Val Asn Glu Ala Phe Ala Asp Gly Gly Gly
                165                 170                 175

Arg Arg Gln Asp Ser Ala Phe Gln Gln Lys Leu Gly Asn Gly Tyr Ile
            180                 185                 190

```
Glu Thr Ala Phe Arg Ala Ala Arg Ala Ala Asp Pro Thr Ala Lys Leu
            195                 200                 205
Cys Ile Asn Asp Tyr Asn Val Glu Gly Ile Asn Ala Lys Ser Asn Ser
    210                 215                 220
Leu Tyr Asp Leu Val Lys Asp Phe Lys Ala Arg Gly Val Pro Leu Asp
225                 230                 235                 240
Cys Val Gly Phe Gln Ser His Leu Ile Val Gly Gln Val Pro Gly Asp
                245                 250                 255
Phe Arg Gln Asn Leu Gln Arg Phe Ala Asp Leu Gly Val Asp Val Arg
            260                 265                 270
Ile Thr Glu Leu Asp Ile Arg Met Arg Thr Pro Ser Asp Ala Thr Lys
        275                 280                 285
Leu Ala Thr Gln Ala Ala Asp Tyr Lys Lys Val Val Gln Ala Cys Met
    290                 295                 300
Gln Val Thr Arg Cys Gln Gly Val Thr Val Trp Gly Ile Thr Asp Lys
305                 310                 315                 320
Tyr Ser Trp Val Pro Asp Val Phe Pro Gly Glu Gly Ala Ala Leu Val
                325                 330                 335
Trp Asp Ala Ser Tyr Ala Lys Lys Pro Ala Tyr Ala Ala Val Met Glu
            340                 345                 350
Ala Phe Gly Ala Ser Pro Thr Pro Thr Pro Thr Pro Thr Pro Thr Thr
        355                 360                 365
Pro Thr Thr Pro Thr Pro Thr Pro Thr Ser Gly Pro Ala Gly Cys Gln
    370                 375                 380
Val Leu Trp Gly Val Asn Gln Trp Asn Thr Gly Phe Thr Ala Asn Val
385                 390                 395                 400
Thr Val Lys Asn Thr Ser Ser Ala Pro Val Asp Gly Trp Thr Leu Thr
                405                 410                 415
Phe Ser Phe Pro Ser Gly Gln Gln Val Thr Gln Ala Trp Ser Ser Thr
            420                 425                 430
Val Thr Gln Ser Gly Ser Ala Val Thr Val Arg Asn Ala Pro Trp Asn
        435                 440                 445
Gly Ser Ile Pro Ala Gly Gly Thr Ala Gln Phe Gly Phe Asn Gly Ser
    450                 455                 460
His Thr Gly Thr Asn Ala Ala Pro Thr Ala Phe Ser Leu Asn Gly Thr
465                 470                 475                 480
Pro Cys Thr Val Gly
                485

<210> SEQ ID NO 2
<211> LENGTH: 393
<212> TYPE: DNA
<213> ORGANISM: Artificial Sequence
<220> FEATURE:
<223> OTHER INFORMATION: Codon optimized nucleotide sequence including
      the Cellomonas fimi exoglucanase CBD

<400> SEQUENCE: 2
ggtgcgtctc ctaccccaac tccaaccacc ccgaccccga ccccgaccac tccgacgcca      60
acgccgacct ctggtccagc gggttgccag gttctgtggg tgttaaccag tggaacacc     120 ggcttcaccg cgaacgttac cgtgaaaaac acctcttctg ccccggttga cggttggacc    180
ctgaccttct ctttcccgtc tggtcagcag gttacccagg cgtggtcttc taccgttacg    240
cagtctggtt ctgcggtgac cgttcgtaac gcgccgtgga atggtccat cccggctggc     300 ggtacggccc agttcggctt aaccggttcc acaccggta ccaatgcggc accgaccgcg      360
```

```
ttctctctga acggtacccc gtgcaccgtt ggt                                    393
```

\<210\> SEQ ID NO 3
\<211\> LENGTH: 369
\<212\> TYPE: PRT
\<213\> ORGANISM: Cellomonas fimi

\<400\> SEQUENCE: 3

```
Met Thr Thr Thr Leu Ser Arg Arg Leu Ala Gly Thr Leu Ala Ala Leu
1               5                   10                  15

Leu Leu Ala Leu Ala Gly Ala Leu Ala Leu Ala Gly Pro Thr Gln Ala
            20                  25                  30

Ala Asp Pro Val Arg Ile Met Pro Leu Gly Asp Ser Ile Thr Gly Asn
        35                  40                  45

Pro Gly Cys Trp Arg Ala Leu Leu Trp Gln Lys Leu Gln Gln Gly Gly
    50                  55                  60

His Thr Asp Val Asp Met Val Gly Thr Leu Pro Ala Gln Gly Cys Gly
65                  70                  75                  80

Val Ala His Asp Gly Asp Asn Glu Gly His Gly Gly Tyr Leu Val Thr
                85                  90                  95

Asp Val Ala Ala Gln Gly Gln Leu Val Gly Trp Leu Ala Ala Thr Asp
            100                 105                 110

Pro Asp Val Val Met His Phe Gly Thr Asn Asp Val Trp Ser Ala
        115                 120                 125

Arg Thr Thr Gln Gln Ile Leu Asp Ala Tyr Thr Thr Leu Val Gln Gln
    130                 135                 140

Met Arg Ala Ser Asn Pro Gln Met Arg Val Leu Val Ala Gln Ile Ile
145                 150                 155                 160

Pro Val Ala Pro Pro Thr Cys Ala Gln Cys Pro Ala Arg Thr Ala Ala
                165                 170                 175

Leu Asn Ala Ala Ile Pro Ala Trp Ala Ala Gly Ile Thr Thr Ala Gln
            180                 185                 190

Ser Pro Val Val Val Asp Gln Ala Thr Gly Trp Val Pro Ala Thr
        195                 200                 205

Asp Thr Ser Asp Gly Val His Pro Asp Glu Asp Gly Ile Val Lys Leu
    210                 215                 220

Ala Asp Arg Trp Tyr Pro Ala Leu Ala Ala Val Leu Asp Gly Thr Thr
225                 230                 235                 240

Pro Thr Pro Thr Pro Thr Pro Thr Val Ser Pro Thr Pro Thr
                245                 250                 255

Pro Thr Pro Thr Pro Ser Val Thr Pro Thr Pro Thr Pro Gly
            260                 265                 270

Gly Ala Thr Cys Thr Ala Ser Tyr Ala Val Ser Ser Gln Trp Gln Gly
        275                 280                 285

Gly Phe Val Ala Ser Val Arg Val Thr Ala Thr Ser Pro Val Ser Ser
    290                 295                 300

Trp Thr Val Ala Val Thr Leu Pro Gly Gly Ala Val Gln His Ala Trp
305                 310                 315                 320

Ser Ala Thr Ala Thr Thr Ser Gly Ser Thr Ala Thr Phe Ala Asn Ala
                325                 330                 335

Ala Trp Asn Gly Thr Leu Ala Ala Gly Gln Gln Ala Asp Leu Gly Phe
            340                 345                 350

Gln Gly Thr Gly Ser Pro Thr Ala Ser Ala Val Thr Cys Thr Ala Thr
        355                 360                 365
```

Arg

<210> SEQ ID NO 4
<211> LENGTH: 378
<212> TYPE: DNA
<213> ORGANISM: Artificial Sequence
<220> FEATURE:
<223> OTHER INFORMATION: Codon optimized nucleotide sequence including the Cellomonas fimi cellulose binding protein CBD

<400> SEQUENCE: 4

```
accactccaa ccccaacgcc gactccgacg cctaccgtta gccctactcc taccccgacc      60
cctacgccgt ctgttacgcc aactccaacc ccaacgcctg gtggtgcgac ctgcaccgca     120
tcttacgcgg ttagctctca gtggcagggc ggttttgttg cgagcgttcg tgttaccgcc     180
acctccccgg tttctagctg gaccgttgcg gttaccctgc cgggtggcgc ggttcaacat     240
gcgtggtctg cgacggcaac cacctctggt tctaccgcga cctttgcgaa cgcggcgtgg     300
aacggtacgc tggctgctgg tcagcaggcg gacctgggct tccagggtac cggctctccg     360
accgcgtctg ccgtaacg                                                   378
```

<210> SEQ ID NO 5
<211> LENGTH: 1853
<212> TYPE: PRT
<213> ORGANISM: Clostridium thermocellum

<400> SEQUENCE: 5

```
Met Arg Lys Val Ile Ser Met Leu Leu Val Val Ala Met Leu Thr Thr
1               5                   10                  15

Ile Phe Ala Ala Met Ile Pro Gln Thr Val Ser Ala Ala Thr Met Thr
            20                  25                  30

Val Glu Ile Gly Lys Val Thr Ala Ala Val Gly Ser Lys Val Glu Ile
        35                  40                  45

Pro Ile Thr Leu Lys Gly Val Pro Ser Lys Gly Met Ala Asn Cys Asp
    50                  55                  60

Phe Val Leu Gly Tyr Asp Pro Asn Val Leu Glu Val Thr Glu Val Lys
65                  70                  75                  80

Pro Gly Ser Ile Ile Lys Asp Pro Asp Pro Ser Lys Ser Phe Asp Ser
                85                  90                  95

Ala Ile Tyr Pro Asp Arg Lys Met Ile Val Phe Leu Phe Ala Glu Asp
            100                 105                 110

Ser Gly Arg Gly Thr Tyr Ala Ile Thr Gln Asp Gly Val Phe Ala Thr
        115                 120                 125

Ile Val Ala Thr Val Lys Ser Ala Ala Ala Pro Ile Thr Leu Leu
    130                 135                 140

Glu Val Gly Ala Phe Ala Asp Asn Asp Leu Val Glu Ile Ser Thr Thr
145                 150                 155                 160

Phe Val Ala Gly Gly Val Asn Leu Gly Ser Ser Val Pro Thr Thr Gln
                165                 170                 175

Pro Asn Val Pro Ser Asp Gly Val Val Val Glu Ile Gly Lys Val Thr
            180                 185                 190

Gly Ser Val Gly Thr Thr Val Glu Ile Pro Val Tyr Phe Arg Gly Val
        195                 200                 205

Pro Ser Lys Gly Ile Ala Asn Cys Asp Phe Val Phe Arg Tyr Asp Pro
    210                 215                 220

Asn Val Leu Glu Ile Ile Gly Ile Asp Pro Gly Asp Ile Ile Val Asp
```

-continued

```
            225                 230                 235                 240
        Pro Asn Pro Thr Lys Ser Phe Asp Thr Ala Ile Tyr Pro Asp Arg Lys
                        245                 250                 255
        Ile Ile Val Phe Leu Phe Ala Glu Asp Ser Gly Thr Gly Ala Tyr Ala
                        260                 265                 270
        Ile Thr Lys Asp Gly Val Phe Ala Lys Ile Arg Ala Thr Val Lys Ser
                        275                 280                 285
        Ser Ala Pro Gly Tyr Ile Thr Phe Asp Glu Val Gly Gly Phe Ala Asp
                        290                 295                 300
        Asn Asp Leu Val Glu Gln Lys Val Ser Phe Ile Asp Gly Val Asn
        305                 310                 315                 320
        Val Gly Asn Ala Thr Pro Thr Lys Gly Ala Thr Pro Thr Asn Thr Ala
                        325                 330                 335
        Thr Pro Thr Lys Ser Ala Thr Ala Thr Pro Thr Arg Pro Ser Val Pro
                        340                 345                 350
        Thr Asn Thr Pro Thr Asn Thr Pro Ala Asn Thr Pro Val Ser Gly Asn
                        355                 360                 365
        Leu Lys Val Glu Phe Tyr Asn Ser Asn Pro Ser Asp Thr Thr Asn Ser
            370                 375                 380
        Ile Asn Pro Gln Phe Lys Val Thr Asn Thr Gly Ser Ser Ala Ile Asp
        385                 390                 395                 400
        Leu Ser Lys Leu Thr Leu Arg Tyr Tyr Tyr Thr Val Asp Gly Gln Lys
                        405                 410                 415
        Asp Gln Thr Phe Trp Cys Asp His Ala Ala Ile Ile Gly Ser Asn Gly
                        420                 425                 430
        Ser Tyr Asn Gly Ile Thr Ser Asn Val Lys Gly Thr Phe Val Lys Met
                        435                 440                 445
        Ser Ser Ser Thr Asn Asn Ala Asp Thr Tyr Leu Glu Ile Ser Phe Thr
            450                 455                 460
        Gly Gly Thr Leu Glu Pro Gly Ala His Val Gln Ile Gln Gly Arg Phe
        465                 470                 475                 480
        Ala Lys Asn Asp Trp Ser Asn Tyr Thr Gln Ser Asn Asp Tyr Ser Phe
                        485                 490                 495
        Lys Ser Ala Ser Gln Phe Val Glu Trp Asp Gln Val Thr Ala Tyr Leu
                        500                 505                 510
        Asn Gly Val Leu Val Trp Gly Lys Glu Pro Gly Gly Ser Val Val Pro
                        515                 520                 525
        Ser Thr Gln Pro Val Thr Thr Pro Ala Thr Thr Lys Pro Pro Ala
            530                 535                 540
        Thr Thr Lys Pro Pro Ala Thr Thr Ile Pro Pro Ser Asp Asp Pro Asn
        545                 550                 555                 560
        Ala Ile Lys Ile Lys Val Asp Thr Val Asn Ala Lys Pro Gly Asp Thr
                        565                 570                 575
        Val Asn Ile Pro Val Arg Phe Ser Gly Ile Pro Ser Lys Gly Ile Ala
                        580                 585                 590
        Asn Cys Asp Phe Val Tyr Ser Tyr Asp Pro Asn Val Leu Glu Ile Ile
                        595                 600                 605
        Glu Ile Lys Pro Gly Glu Leu Ile Val Asp Pro Asn Pro Asp Lys Ser
                        610                 615                 620
        Phe Asp Thr Ala Val Tyr Pro Asp Arg Lys Ile Ile Val Phe Leu Phe
        625                 630                 635                 640
        Ala Glu Asp Ser Gly Thr Gly Ala Tyr Ala Ile Thr Lys Asp Gly Val
                        645                 650                 655
```

-continued

Phe Ala Thr Ile Val Ala Lys Val Lys Ser Gly Ala Pro Asn Gly Leu
            660                 665                 670

Ser Val Ile Lys Phe Val Glu Val Gly Gly Phe Ala Asn Asn Asp Leu
            675                 680                 685

Val Glu Gln Arg Thr Gln Phe Phe Asp Gly Gly Val Asn Val Gly Asp
            690                 695                 700

Thr Thr Val Pro Thr Thr Pro Thr Thr Pro Val Thr Thr Pro Thr Asp
705                 710                 715                 720

Asp Ser Asn Ala Val Arg Ile Lys Val Asp Thr Val Asn Ala Lys Pro
                725                 730                 735

Gly Asp Thr Val Arg Ile Pro Val Arg Phe Ser Gly Ile Pro Ser Lys
                740                 745                 750

Gly Ile Ala Asn Cys Asp Phe Val Tyr Ser Tyr Asp Pro Asn Val Leu
                755                 760                 765

Glu Ile Ile Glu Ile Glu Pro Gly Asp Ile Ile Val Asp Pro Asn Pro
                770                 775                 780

Asp Lys Ser Phe Asp Thr Ala Val Tyr Pro Asp Arg Lys Ile Ile Val
785                 790                 795                 800

Phe Leu Phe Ala Glu Asp Ser Gly Thr Gly Ala Tyr Ala Ile Thr Lys
                805                 810                 815

Asp Gly Val Phe Ala Thr Ile Val Ala Lys Val Lys Ser Gly Ala Pro
                820                 825                 830

Asn Gly Leu Ser Val Ile Lys Phe Val Glu Val Gly Gly Phe Ala Asn
                835                 840                 845

Asn Asp Leu Val Glu Gln Lys Thr Gln Phe Phe Asp Gly Gly Val Asn
                850                 855                 860

Val Gly Asp Thr Thr Glu Pro Ala Thr Pro Thr Thr Pro Val Thr Thr
865                 870                 875                 880

Pro Thr Thr Thr Asp Asp Leu Asp Ala Val Arg Ile Lys Val Asp Thr
                885                 890                 895

Val Asn Ala Lys Pro Gly Asp Thr Val Arg Ile Pro Val Arg Phe Ser
                900                 905                 910

Gly Ile Pro Ser Lys Gly Ile Ala Asn Cys Asp Phe Val Tyr Ser Tyr
                915                 920                 925

Asp Pro Asn Val Leu Glu Ile Ile Glu Ile Glu Pro Gly Asp Ile Ile
                930                 935                 940

Val Asp Pro Asn Pro Asp Lys Ser Phe Asp Thr Ala Val Tyr Pro Asp
945                 950                 955                 960

Arg Lys Ile Ile Val Phe Leu Phe Ala Glu Asp Ser Gly Thr Gly Ala
                965                 970                 975

Tyr Ala Ile Thr Lys Asp Gly Val Phe Ala Thr Ile Val Ala Lys Val
                980                 985                 990

Lys Ser Gly Ala Pro Asn Gly Leu Ser Val Ile Lys Phe Val Glu Val
                995                 1000                1005

Gly Gly Phe Ala Asn Asn Asp Leu Val Glu Gln Lys Thr Gln Phe
            1010                1015                1020

Phe Asp Gly Gly Val Asn Val Gly Asp Thr Thr Glu Pro Ala Thr
            1025                1030                1035

Pro Thr Thr Pro Val Thr Thr Pro Thr Thr Thr Asp Asp Leu Asp
            1040                1045                1050

Ala Val Arg Ile Lys Val Asp Thr Val Asn Ala Lys Pro Gly Asp
            1055                1060                1065

-continued

Thr Val Arg Ile Pro Val Arg Phe Ser Gly Ile Pro Ser Lys Gly
1070                1075                1080

Ile Ala Asn Cys Asp Phe Val Tyr Ser Tyr Asp Pro Asn Val Leu
1085                1090                1095

Glu Ile Ile Glu Ile Glu Pro Gly Asp Ile Ile Val Asp Pro Asn
1100                1105                1110

Pro Asp Lys Ser Phe Asp Thr Ala Val Tyr Pro Asp Arg Lys Ile
1115                1120                1125

Ile Val Phe Leu Phe Ala Glu Asp Ser Gly Thr Gly Ala Tyr Ala
1130                1135                1140

Ile Thr Lys Asp Gly Val Phe Ala Thr Ile Val Ala Lys Val Lys
1145                1150                1155

Glu Gly Ala Pro Asn Gly Leu Ser Val Ile Lys Phe Val Glu Val
1160                1165                1170

Gly Gly Phe Ala Asn Asn Asp Leu Val Glu Gln Lys Thr Gln Phe
1175                1180                1185

Phe Asp Gly Gly Val Asn Val Gly Asp Thr Thr Glu Pro Ala Thr
1190                1195                1200

Pro Thr Thr Pro Val Thr Thr Pro Thr Thr Thr Asp Asp Leu Asp
1205                1210                1215

Ala Val Arg Ile Lys Val Asp Thr Val Asn Ala Lys Pro Gly Asp
1220                1225                1230

Thr Val Arg Ile Pro Val Arg Phe Ser Gly Ile Pro Ser Lys Gly
1235                1240                1245

Ile Ala Asn Cys Asp Phe Val Tyr Ser Tyr Asp Pro Asn Val Leu
1250                1255                1260

Glu Ile Ile Glu Ile Glu Pro Gly Glu Leu Ile Val Asp Pro Asn
1265                1270                1275

Pro Thr Lys Ser Phe Asp Thr Ala Val Tyr Pro Asp Arg Lys Met
1280                1285                1290

Ile Val Phe Leu Phe Ala Glu Asp Ser Gly Thr Gly Ala Tyr Ala
1295                1300                1305

Ile Thr Glu Asp Gly Val Phe Ala Thr Ile Val Ala Lys Val Lys
1310                1315                1320

Ser Gly Ala Pro Asn Gly Leu Ser Val Ile Lys Phe Val Glu Val
1325                1330                1335

Gly Gly Phe Ala Asn Asn Asp Leu Val Glu Gln Lys Thr Gln Phe
1340                1345                1350

Phe Asp Gly Gly Val Asn Val Gly Asp Thr Thr Glu Pro Ala Thr
1355                1360                1365

Pro Thr Thr Pro Val Thr Thr Pro Thr Thr Thr Asp Asp Leu Asp
1370                1375                1380

Ala Val Arg Ile Lys Val Asp Thr Val Asn Ala Lys Pro Gly Asp
1385                1390                1395

Thr Val Arg Ile Pro Val Arg Phe Ser Gly Ile Pro Ser Lys Gly
1400                1405                1410

Ile Ala Asn Cys Asp Phe Val Tyr Ser Tyr Asp Pro Asn Val Leu
1415                1420                1425

Glu Ile Ile Glu Ile Glu Pro Gly Asp Ile Ile Val Asp Pro Asn
1430                1435                1440

Pro Asp Lys Ser Phe Asp Thr Ala Val Tyr Pro Asp Arg Lys Ile
1445                1450                1455

Ile Val Phe Leu Phe Ala Glu Asp Ser Gly Thr Gly Ala Tyr Ala

-continued

```
            1460                1465                1470

Ile Thr Lys Asp Gly Val Phe Ala Thr Ile Val Ala Lys Val Lys
        1475                1480                1485

Glu Gly Ala Pro Asn Gly Leu Ser Val Ile Lys Phe Val Glu Val
        1490                1495                1500

Gly Gly Phe Ala Asn Asn Asp Leu Val Glu Gln Lys Thr Gln Phe
        1505                1510                1515

Phe Asp Gly Gly Val Asn Val Gly Asp Thr Thr Val Pro Thr Thr
        1520                1525                1530

Ser Pro Thr Thr Thr Pro Pro Glu Pro Thr Ile Thr Pro Asn Lys
        1535                1540                1545

Leu Thr Leu Lys Ile Gly Arg Ala Glu Gly Arg Pro Gly Asp Thr
        1550                1555                1560

Val Glu Ile Pro Val Asn Leu Tyr Gly Val Pro Gln Lys Gly Ile
        1565                1570                1575

Ala Ser Gly Asp Phe Val Val Ser Tyr Asp Pro Asn Val Leu Glu
        1580                1585                1590

Ile Ile Glu Ile Glu Pro Gly Glu Leu Ile Val Asp Pro Asn Pro
        1595                1600                1605

Thr Lys Ser Phe Asp Thr Ala Val Tyr Pro Asp Arg Lys Met Ile
        1610                1615                1620

Val Phe Leu Phe Ala Glu Asp Ser Gly Thr Gly Ala Tyr Ala Ile
        1625                1630                1635

Thr Glu Asp Gly Val Phe Ala Thr Ile Val Ala Lys Val Lys Glu
        1640                1645                1650

Gly Ala Pro Glu Gly Phe Ser Ala Ile Glu Ile Ser Glu Phe Gly
        1655                1660                1665

Ala Phe Ala Asp Asn Asp Leu Val Glu Val Glu Thr Asp Leu Ile
        1670                1675                1680

Asn Gly Gly Val Leu Val Thr Asn Lys Pro Val Ile Glu Gly Tyr
        1685                1690                1695

Lys Val Ser Gly Tyr Ile Leu Pro Asp Phe Ser Phe Asp Ala Thr
        1700                1705                1710

Val Ala Pro Leu Val Lys Ala Gly Phe Lys Val Glu Ile Val Gly
        1715                1720                1725

Thr Glu Leu Tyr Ala Val Thr Asp Ala Asn Gly Tyr Phe Glu Ile
        1730                1735                1740

Thr Gly Val Pro Ala Asn Ala Ser Gly Tyr Thr Leu Lys Ile Ser
        1745                1750                1755

Arg Ala Thr Tyr Leu Asp Arg Val Ile Ala Asn Val Val Val Thr
        1760                1765                1770

Gly Asp Thr Ser Val Ser Thr Ser Gln Ala Pro Ile Met Met Trp
        1775                1780                1785

Val Gly Asp Ile Val Lys Asp Asn Ser Ile Asn Leu Leu Asp Val
        1790                1795                1800

Ala Glu Val Ile Arg Cys Phe Asn Ala Thr Lys Gly Ser Ala Asn
        1805                1810                1815

Tyr Val Glu Glu Leu Asp Ile Asn Arg Asn Gly Ala Ile Asn Met
        1820                1825                1830

Gln Asp Ile Met Ile Val His Lys His Phe Gly Ala Thr Ser Ser
        1835                1840                1845

Asp Tyr Asp Ala Gln
        1850
```

```
<210> SEQ ID NO 6
<211> LENGTH: 772
<212> TYPE: PRT
<213> ORGANISM: Clostridium thermocellum

<400> SEQUENCE: 6
```

| | | | | | | | | | | | | | | |
|---|---|---|---|---|---|---|---|---|---|---|---|---|---|---|
| Asp | Pro | Ser | Lys | Ser | Phe | Asp | Ser | Ala | Ile | Tyr | Pro | Asp | Arg | Lys | Met |
| 1 | | | | 5 | | | | | 10 | | | | | 15 | |
| Ile | Val | Phe | Leu | Phe | Ala | Glu | Asp | Ser | Gly | Arg | Gly | Thr | Tyr | Ala | Ile |
| | | | 20 | | | | | 25 | | | | | 30 | | |
| Thr | Gln | Asp | Gly | Val | Phe | Ala | Thr | Ile | Val | Ala | Thr | Val | Lys | Ser | Ala |
| | | 35 | | | | | 40 | | | | | 45 | | | |
| Ala | Ala | Ala | Pro | Ile | Thr | Leu | Leu | Glu | Val | Gly | Ala | Phe | Arg | Asp | Asn |
| | 50 | | | | | 55 | | | | | 60 | | | | |
| Asp | Leu | Val | Glu | Ile | Ser | Thr | Thr | Phe | Val | Ala | Gly | Val | Asn | Leu | |
| 65 | | | | | 70 | | | | 75 | | | | | 80 | |
| Gly | Ser | Ser | Val | Pro | Thr | Thr | Gln | Pro | Asn | Val | Pro | Ser | Asp | Gly | Val |
| | | | | 85 | | | | | 90 | | | | | 95 | |
| Val | Val | Glu | Ile | Gly | Lys | Val | Thr | Gly | Ser | Val | Gly | Thr | Thr | Val | Glu |
| | | | 100 | | | | | 105 | | | | | 110 | | |
| Ile | Pro | Val | Tyr | Phe | Arg | Gly | Val | Pro | Ser | Lys | Gly | Ile | Ala | Asn | Cys |
| | | 115 | | | | | 120 | | | | | 125 | | | |
| Asp | Phe | Val | Phe | Arg | Tyr | Asp | Pro | Asn | Val | Leu | Glu | Ile | Ile | Gly | Ile |
| | 130 | | | | | 135 | | | | | 140 | | | | |
| Asp | Pro | Arg | Ser | Ile | Ile | Val | Asp | Pro | Asn | Pro | Thr | Lys | Ser | Phe | Asp |
| 145 | | | | | 150 | | | | 155 | | | | | 160 | |
| Thr | Ala | Ile | Tyr | Ala | Asp | Arg | Lys | Ile | Ile | Val | Phe | Leu | Phe | Cys | Gly |
| | | | | 165 | | | | | 170 | | | | | 175 | |
| Arg | Gln | Arg | Asn | Arg | Ser | Val | Ser | Ile | Thr | Lys | Asp | Gly | Val | Phe | Ala |
| | | | 180 | | | | | 185 | | | | | 190 | | |
| Lys | Ile | Arg | Ala | Thr | Val | Lys | Ser | Ser | Ala | Pro | Ala | Tyr | Ile | Thr | Phe |
| | | 195 | | | | | 200 | | | | | 205 | | | |
| Asp | Glu | Val | Gly | Gly | Phe | Ala | Asp | Asn | Asp | Leu | Val | Glu | Gln | Lys | Val |
| | 210 | | | | | 215 | | | | | 220 | | | | |
| Ser | Phe | Ile | Asp | Gly | Gly | Val | Asn | Val | Gly | Asn | Ala | Thr | Pro | Thr | Lys |
| 225 | | | | | 230 | | | | 235 | | | | | 240 | |
| Gly | Ala | Thr | Pro | Thr | Asn | Thr | Ala | Thr | Pro | Thr | Lys | Ser | Ala | Thr | Ala |
| | | | | 245 | | | | | 250 | | | | | 255 | |
| Thr | Pro | Pro | Gly | His | Ser | Val | Pro | Thr | Asn | Thr | Pro | Thr | Asn | Thr | Pro |
| | | | 260 | | | | | 265 | | | | | 270 | | |
| Ala | Asn | Thr | Pro | Val | Ser | Gly | Asn | Leu | Lys | Val | Glu | Phe | Tyr | Asn | Ser |
| | | 275 | | | | | 280 | | | | | 285 | | | |
| Asn | Pro | Ser | Asp | Thr | Thr | Asn | Ser | Ile | Asn | Pro | Gln | Phe | Lys | Val | Thr |
| | 290 | | | | | 295 | | | | | 300 | | | | |
| Asn | Thr | Gly | Ser | Ser | Ala | Ile | Asp | Leu | Ser | Lys | Leu | Thr | Leu | Arg | Tyr |
| 305 | | | | | 310 | | | | 315 | | | | | 320 | |
| Tyr | Tyr | Thr | Val | Asp | Gly | Gln | Lys | Asp | Gln | Thr | Phe | Trp | Cys | Asp | His |
| | | | | 325 | | | | | 330 | | | | | 335 | |
| Ala | Ala | Ile | Ile | Gly | Ser | Asn | Gly | Ser | Tyr | Asn | Gly | Ile | Thr | Ser | Asn |
| | | | 340 | | | | | 345 | | | | | 350 | | |
| Val | Lys | Gly | Thr | Phe | Val | Lys | Met | Ser | Ser | Ser | Thr | Asn | Asn | Ala | Asp |
| | | 355 | | | | | 360 | | | | | 365 | | | |
| Thr | Tyr | Leu | Glu | Ile | Ser | Phe | Thr | Gly | Gly | Thr | Leu | Glu | Pro | Gly | Ala |

```
                370                 375                 380
His Val Gln Ile Gln Gly Arg Phe Ala Lys Asn Asp Trp Ser Asn Tyr
385                 390                 395                 400

Thr Gln Ser Asn Asp Tyr Ser Phe Lys Ser Arg Ser Gln Phe Val Glu
                405                 410                 415

Trp Asp Gln Val Thr Ala Tyr Leu Asn Gly Val Leu Val Trp Gly Lys
                420                 425                 430

Glu Pro Gly Gly Ser Val Val Pro Ser Thr Gln Pro Val Thr Thr Pro
                435                 440                 445

Pro Ala Thr Thr Lys Pro Pro Ala Thr Thr Ile Pro Pro Ser Asp Asp
450                 455                 460

Pro Asn Ala Ile Lys Ile Lys Val Asp Thr Val Asn Ala Lys Pro Gly
465                 470                 475                 480

Asp Thr Val Asn Ile Pro Val Arg Phe Ser Gly Ile Pro Ser Lys Gly
                485                 490                 495

Ile Ala Asn Cys Asp Phe Val Tyr Ser Tyr Asp Pro Asn Val Leu Glu
                500                 505                 510

Ile Ile Glu Ile Lys Pro Gly Glu Leu Ile Val Asp Pro Asn Pro Asp
                515                 520                 525

Lys Ser Phe Asp Thr Ala Val Tyr Pro Asp Arg Lys Met Ile Val Phe
                530                 535                 540

Leu Phe Ala Glu Asp Ser Gly Thr Gly Ala Tyr Ala Ile Thr Glu Asp
545                 550                 555                 560

Gly Val Phe Ala Thr Ile Val Ala Lys Val Lys Glu Gly Ala Pro Glu
                565                 570                 575

Gly Phe Ser Ala Ile Glu Ile Ser Glu Phe Gly Ala Phe Ala Asp Asn
                580                 585                 590

Asp Leu Val Glu Val Glu Thr Asp Leu Ile Asn Gly Gly Val Leu Val
                595                 600                 605

Thr Asn Lys Pro Val Ile Glu Gly Tyr Lys Val Ser Gly Tyr Ile Leu
610                 615                 620

Pro Asp Phe Ser Phe Asp Ala Thr Val Ala Pro Leu Val Lys Ala Gly
625                 630                 635                 640

Phe Lys Val Glu Ile Val Gly Thr Glu Leu Tyr Ala Val Thr Asp Ala
                645                 650                 655

Asn Gly Tyr Phe Glu Ile Thr Gly Val Pro Ala Asn Ala Ser Gly Tyr
                660                 665                 670

Thr Leu Lys Ile Ser Arg Ala Thr Tyr Leu Asp Arg Val Ile Ala Asn
                675                 680                 685

Val Val Val Thr Gly Asp Thr Ser Val Ser Thr Ser Gln Ala Pro Ile
                690                 695                 700

Met Met Trp Val Gly Asp Ile Val Lys Asp Asn Ser Ile Asn Leu Leu
705                 710                 715                 720

Asp Val Ala Glu Val Ile Arg Cys Phe Asn Ala Thr Lys Gly Ser Ala
                725                 730                 735

Asn Tyr Val Glu Glu Leu Asp Ile Asn Arg Asn Gly Ala Ile Asn Met
                740                 745                 750

Gln Asp Ile Met Ile Val His Lys His Phe Gly Ala Thr Ser Ser Asp
                755                 760                 765

Tyr Asp Ala Gln
    770

<210> SEQ ID NO 7
```

<211> LENGTH: 513
<212> TYPE: PRT
<213> ORGANISM: Trichoderma reesei

<400> SEQUENCE: 7

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
```

-continued

```
                385                 390                 395                 400
Asn Glu Thr Ser Ser Thr Pro Gly Ala Val Arg Gly Ser Cys Ser Thr
                    405                 410                 415

Ser Ser Gly Val Pro Ala Gln Val Glu Ser Gln Ser Pro Asn Ala Lys
                420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Arg Gly Thr Thr Thr
        450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu Asn Pro Tyr Tyr Ser Gln Cys
                500                 505                 510

Leu

<210> SEQ ID NO 8
<211> LENGTH: 192
<212> TYPE: DNA
<213> ORGANISM: Artificial Sequence
<220> FEATURE:
<223> OTHER INFORMATION: Codon optimized nucleotide sequence including
      the Trichoderma reesei cellobiohydrylase ICBD

<400> SEQUENCE: 8
tctggtggta acccgccagg tggcaaccgt ggcaccacca ctacgcgtcg tccggcgact    60
acgaccggtt cttctccggg tccgacgcag tctcactacg gtcagtgcgg tggtatcggt   120
tactctggcc cgaccgtttg cgcgtctggt acgacctgcc aggttctgaa cccgtactac   180
tctcagtgcc tg                                                       192

<210> SEQ ID NO 9
<211> LENGTH: 471
<212> TYPE: PRT
<213> ORGANISM: Trichoderma reesei

<400> SEQUENCE: 9

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
                20                  25                  30

Gln Cys Gly Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
        50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140
```

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
            165                 170                 175

Arg Thr Ala Asn Lys Asn Gly Asn Tyr Ala Gly Gln Phe Val Val
            180                 185                 190

Tyr Asp Leu Pro Asp Arg Asp Cys Ala Ala Leu Ala Ser Asn Gly Glu
            195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
            275                 280                 285

Gly His Ala Gly Trp Leu Gly Trp Pro Ala Asn Gln Asp Pro Ala Ala
290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
            355                 360                 365

Ala Phe Phe Ile Thr Asp Gln Gly Arg Ser Gly Lys Gln Pro Thr Gly
370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
            435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 10
<211> LENGTH: 231
<212> TYPE: DNA
<213> ORGANISM: Artificial Sequence
<220> FEATURE:
<223> OTHER INFORMATION: Codon optimized nucleotide sequence including
      the Trichoderma reesei cellobiohydrylase IICBD

<400> SEQUENCE: 10
gtttggggtc agtgcggtgg tcagaactgg tctggtccga cctgctgcgc gtctggttct      60
acctgcgttt actctaacga ctactactct cagtgcctgc gggtgctgc gtcttctagc      120 tcttctaccc gtgcggcgtc taccacctct cgtgtgtctc gactacctc ccgttcttct     180 tctgcgaccc caccgccagg ctctactacc actcgtgttc cgccggttgg t      231

<210> SEQ ID NO 11
<211> LENGTH: 611
<212> TYPE: PRT
<213> ORGANISM: Cellvibrio japonicas

<400> SEQUENCE: 11

Met Arg Thr Ala Met Ala Lys Ser Leu Gly Ala Ala Phe Leu Gly
1               5                   10                  15

Ala Ala Leu Phe Ala His Thr Leu Ala Ala Gln Thr Ala Thr Cys Ser
            20                  25                  30

Tyr Asn Ile Thr Asn Glu Trp Asn Thr Gly Tyr Thr Gly Asp Ile Thr
                35                  40                  45

Ile Thr Asn Arg Gly Ser Ala Ile Asn Gly Trp Ser Val Asn Trp
    50                  55                  60

Gln Tyr Ala Thr Asn Arg Leu Ser Ser Ser Trp Asn Ala Asn Val Ser
65                  70                  75                  80

Gly Ser Asn Pro Tyr Ser Ala Ser Asn Leu Ser Trp Asn Gly Asn Ile
                85                  90                  95

Gln Pro Gly Gln Ser Val Ser Phe Gly Phe Gln Val Asn Lys Asn Gly
            100                 105                 110

Gly Ser Ala Glu Arg Pro Ser Val Gly Gly Ser Ile Cys Ser Gly Ser
            115                 120                 125

Val Ala Ser Ser Ser Ala Pro Ala Ser Val Pro Ser Ser Ile Ala
    130                 135                 140

Ser Ser Ser Pro Ser Ser Val Ala Ser Ser Val Ile Ser Ser Met Ala
145                 150                 155                 160

Ser Ser Ser Pro Val Ser Ser Ser Val Ala Ser Ser Thr Pro Gly
                165                 170                 175

Ser Ser Ser Gly Asn Gln Gln Cys Asn Trp Tyr Gly Thr Leu Tyr Pro
            180                 185                 190

Leu Cys Val Thr Thr Thr Asn Gly Trp Gly Trp Glu Asp Gln Arg Ser
            195                 200                 205

Cys Ile Ala Arg Ser Thr Cys Ala Ala Gln Pro Ala Pro Phe Gly Ile
    210                 215                 220

Val Gly Ser Gly Ser Ser Thr Pro Val Ser Ser Ser Ser Ser Ser Leu
225                 230                 235                 240

Ser Ser Ser Ser Val Val Ser Ser Ile Arg Ser Ser Ser Ser Ser
                245                 250                 255

Ser Ser Ser Val Ala Thr Gly Asn Gly Leu Ala Ser Leu Ala Asp Phe
            260                 265                 270

Pro Ile Gly Val Ala Val Ala Ala Ser Gly Gly Asn Ala Asp Ile Phe
    275                 280                 285

Thr Ser Ser Ala Arg Gln Asn Ile Val Arg Ala Glu Phe Asn Gln Ile
    290                 295                 300

Thr Ala Glu Asn Ile Met Lys Met Ser Tyr Met Tyr Ser Gly Ser Asn
305                 310                 315                 320

Phe Ser Phe Thr Asn Ser Asp Arg Leu Val Ser Trp Ala Ala Gln Asn
                325                 330                 335

Gly Gln Thr Val His Gly His Ala Leu Val Trp His Pro Ser Tyr Gln
            340                 345                 350

Leu Pro Asn Trp Ala Ser Asp Ser Asn Ala Asn Phe Arg Gln Asp Phe
            355                 360                 365

Ala Arg His Ile Asp Thr Val Ala Ala His Phe Ala Gly Gln Val Lys
    370                 375                 380

Ser Trp Asp Val Val Asn Glu Ala Leu Phe Asp Ser Ala Asp Asp Pro
385                 390                 395                 400

Asp Gly Arg Gly Ser Ala Asn Gly Tyr Arg Gln Ser Val Phe Tyr Arg
            405                 410                 415

Gln Phe Gly Gly Pro Glu Tyr Ile Asp Glu Ala Phe Arg Arg Ala Arg
            420                 425                 430

Ala Ala Asp Pro Thr Ala Glu Leu Tyr Tyr Asn Asp Phe Asn Thr Glu
            435                 440                 445

Glu Asn Gly Ala Lys Thr Thr Ala Leu Val Asn Leu Val Gln Arg Leu
    450                 455                 460

Leu Asn Asn Gly Val Pro Ile Asp Gly Val Gly Phe Gln Met His Val
465                 470                 475                 480

Met Asn Asp Tyr Pro Ser Ile Ala Asn Ile Arg Gln Ala Met Gln Lys
            485                 490                 495

Ile Val Ala Leu Ser Pro Thr Leu Lys Ile Lys Ile Thr Glu Leu Asp
            500                 505                 510

Val Arg Leu Asn Asn Pro Tyr Asp Gly Asn Ser Ser Asn Asp Tyr Thr
    515                 520                 525

Asn Arg Asn Asp Cys Ala Val Ser Cys Ala Gly Leu Asp Arg Gln Lys
530                 535                 540

Ala Arg Tyr Lys Glu Ile Val Gln Ala Tyr Leu Glu Val Val Pro Pro
545                 550                 555                 560

Gly Arg Arg Gly Gly Ile Thr Val Trp Gly Ile Ala Asp Pro Asp Ser
            565                 570                 575

Trp Leu Tyr Thr His Gln Asn Leu Pro Asp Trp Pro Leu Leu Phe Asn
            580                 585                 590

Asp Asn Leu Gln Pro Lys Pro Ala Tyr Gln Gly Val Val Glu Ala Leu
            595                 600                 605

Ser Gly Arg
    610

<210> SEQ ID NO 12
<211> LENGTH: 465
<212> TYPE: DNA
<213> ORGANISM: Artificial Sequence
<220> FEATURE:
<223> OTHER INFORMATION: Codon optimized nucleotide sequence including
      the Cellvibrio japonicas XynA CBD

<400> SEQUENCE: 12
gcgacctgct cttacaacat caccaacgaa tggaacaccg gttacaccgg cgacattacc    60
atcactaatc gtggttcttc tgcgatcaac ggttggtctg ttaactggca atatgctacg   120
aaccgcctgt cttctagctg gaacgcgaac gtttctggtt ctaacccgta ctctgcgtct   180
aacctctctt ggaacggtaa catccagccg ggtcagtctg tttcctttgg tttccaggtt   240
aacaaaaacg gcggctctgc tgagcgtccg tctgttggtg gtagcatctg ctctggctct   300
gttgcgtcct cttccgcgcc agcttcttcc gtcccatctt ctatcgcgtc ttcttctccg   360
tctagcgttg cctccagcgt tatctcttcc atggcgtcca gctctccggt tagctccagc   420
agcgtagcga gcagcacccc gggtagcagc tctggtaatc agcag                   465

<210> SEQ ID NO 13
<211> LENGTH: 105

```
<212> TYPE: PRT
<213> ORGANISM: Cellomonas fimi

<400> SEQUENCE: 13

Ser Gly Pro Ala Gly Cys Gln Val Leu Trp Gly Val Asn Gln Trp Asn
1               5                   10                  15

Thr Gly Phe Thr Ala Asn Val Thr Val Lys Asn Thr Ser Ser Ala Pro
            20                  25                  30

Val Asp Gly Trp Thr Leu Thr Phe Ser Phe Pro Ser Gly Gln Gln Val
        35                  40                  45

Thr Gln Ala Trp Ser Ser Thr Val Thr Gln Ser Gly Ser Ala Val Thr
    50                  55                  60

Val Arg Asn Ala Pro Trp Asn Gly Ser Ile Pro Ala Gly Gly Thr Ala
65                  70                  75                  80

Gln Phe Gly Phe Asn Gly Ser His Thr Gly Thr Asn Ala Ala Pro Thr
                85                  90                  95

Ala Phe Ser Leu Asn Gly Thr Pro Cys
            100                 105

<210> SEQ ID NO 14
<211> LENGTH: 90
<212> TYPE: PRT
<213> ORGANISM: Cellomonas fimi

<400> SEQUENCE: 14

Thr Cys Thr Ala Ser Tyr Ala Val Ser Ser Gln Trp Gln Gly Gly Phe
1               5                   10                  15

Val Ala Ser Val Arg Val Thr Ala Ser Pro Val Ser Ser Trp Thr
            20                  25                  30

Val Ala Val Thr Leu Pro Gly Gly Ala Val Gln His Ala Trp Ser Ala
        35                  40                  45

Thr Ala Thr Thr Ser Gly Ser Thr Ala Thr Phe Ala Asn Ala Ala Trp
    50                  55                  60

Asn Gly Thr Leu Ala Ala Gly Gln Gln Ala Asp Leu Gly Phe Gln Gly
65                  70                  75                  80

Thr Gly Ser Pro Thr Ala Ser Ala Val Thr
                85                  90

<210> SEQ ID NO 15
<211> LENGTH: 92
<212> TYPE: PRT
<213> ORGANISM: Clostridium thermocellum

<400> SEQUENCE: 15

Val Glu Phe Tyr Asn Ser Asn Pro Ser Asp Thr Thr Asn Ser Ile Asn
1               5                   10                  15

Pro Gln Phe Lys Val Thr Asn Thr Gly Ser Ser Ala Ile Asp Leu Ser
            20                  25                  30

Lys Leu Thr Leu Arg Tyr Tyr Tyr Thr Val Asp Gly Gln Lys Asp Gln
        35                  40                  45

Thr Phe Trp Cys Asp His Ala Ala Ile Ile Gly Ser Asn Gly Ser Tyr
    50                  55                  60

Asn Gly Ile Thr Ser Asn Val Lys Gly Thr Phe Val Lys Met Ser Ser
65                  70                  75                  80

Ser Thr Asn Asn Ala Asp Thr Tyr Leu Glu Ile Ser
                85                  90
```

```
<210> SEQ ID NO 16
<211> LENGTH: 92
<212> TYPE: PRT
<213> ORGANISM: Clostridium thermocellum

<400> SEQUENCE: 16

Val Glu Phe Tyr Asn Ser Asn Pro Ser Asp Thr Thr Asn Ser Ile Asn
1               5                   10                  15

Pro Gln Phe Lys Val Thr Asn Thr Gly Ser Ser Ala Ile Asp Leu Ser
            20                  25                  30

Lys Leu Thr Leu Arg Tyr Tyr Tyr Thr Val Asp Gly Gln Lys Asp Gln
        35                  40                  45

Thr Phe Trp Cys Asp His Ala Ala Ile Ile Gly Ser Asn Gly Ser Tyr
50                  55                  60

Asn Gly Ile Thr Ser Asn Val Lys Gly Thr Phe Val Lys Met Ser Ser
65                  70                  75                  80

Ser Thr Asn Asn Ala Asp Thr Tyr Leu Glu Ile Ser
                85                  90

<210> SEQ ID NO 17
<211> LENGTH: 31
<212> TYPE: PRT
<213> ORGANISM: Trichoderma reesei

<400> SEQUENCE: 17

His Tyr Gly Gln Cys Gly Gly Ile Gly Tyr Ser Gly Pro Thr Val Cys
1               5                   10                  15

Ala Ser Gly Thr Thr Cys Gln Val Leu Asn Pro Tyr Tyr Ser Gln
            20                  25                  30

<210> SEQ ID NO 18
<211> LENGTH: 30
<212> TYPE: PRT
<213> ORGANISM: Trichoderma reesei

<400> SEQUENCE: 18

Val Trp Gly Gln Cys Gly Gly Gln Asn Trp Ser Gly Pro Thr Cys Cys
1               5                   10                  15

Ala Ser Gly Ser Thr Cys Val Tyr Ser Asn Asp Tyr Tyr Ser
            20                  25                  30

<210> SEQ ID NO 19
<211> LENGTH: 42
<212> TYPE: PRT
<213> ORGANISM: Cellvibrio japonicas

<400> SEQUENCE: 19

Ala Thr Cys Ser Tyr Asn Ile Thr Asn Glu Trp Asn Thr Gly Tyr Thr
1               5                   10                  15

Gly Asp Ile Thr Ile Thr Asn Arg Gly Ser Ser Ala Ile Asn Gly Trp
            20                  25                  30

Ser Val Asn Trp Gln Tyr Ala Thr Asn Arg
            35                  40

<210> SEQ ID NO 20
<211> LENGTH: 715
<212> TYPE: PRT
<213> ORGANISM: Escherichia coli

<400> SEQUENCE: 20

Met Asn Val Ile Ala Ile Leu Asn His Met Gly Val Tyr Phe Lys Glu
```

-continued

```
1               5                  10                 15
Glu Pro Ile Arg Glu Leu His Arg Ala Leu Glu Arg Leu Asn Phe Gln
                20                 25                 30
Ile Val Tyr Pro Asn Asp Arg Asp Leu Leu Lys Leu Ile Glu Asn
                35                 40                 45
Asn Ala Arg Leu Cys Gly Val Ile Phe Asp Trp Asp Lys Tyr Asn Leu
50                      55                 60
Glu Leu Cys Glu Glu Ile Ser Lys Met Asn Glu Asn Leu Pro Leu Tyr
65                      70                 75                 80
Ala Phe Ala Asn Thr Tyr Ser Thr Leu Asp Val Ser Leu Asn Asp Leu
                85                 90                 95
Arg Leu Gln Ile Ser Phe Phe Glu Tyr Ala Leu Gly Ala Ala Glu Asp
                100                105                110
Ile Ala Asn Lys Ile Lys Gln Thr Thr Asp Glu Tyr Ile Asn Thr Ile
                115                120                125
Leu Pro Pro Leu Thr Lys Ala Leu Phe Lys Tyr Val Arg Glu Gly Lys
                130                135                140
Tyr Thr Phe Cys Thr Pro Gly His Met Gly Gly Thr Ala Phe Gln Lys
145                     150                155                160
Ser Pro Val Gly Ser Leu Phe Tyr Asp Phe Phe Gly Pro Asn Thr Met
                165                170                175
Lys Ser Asp Ile Ser Ile Ser Val Ser Glu Leu Gly Ser Leu Leu Asp
                180                185                190
His Ser Gly Pro His Lys Glu Ala Glu Gln Tyr Ile Ala Arg Val Phe
                195                200                205
Asn Ala Asp Arg Ser Tyr Met Val Thr Asn Gly Thr Ser Thr Ala Asn
210                     215                220
Lys Ile Val Gly Met Tyr Ser Ala Pro Ala Gly Ser Thr Ile Leu Ile
225                     230                235                240
Asp Arg Asn Cys His Lys Ser Leu Thr His Leu Met Met Met Ser Asp
                245                250                255
Val Thr Pro Ile Tyr Phe Arg Pro Thr Arg Asn Ala Tyr Gly Ile Leu
                260                265                270
Gly Gly Ile Pro Gln Ser Glu Phe Gln His Ala Thr Ile Ala Lys Arg
                275                280                285
Val Lys Glu Thr Pro Asn Ala Thr Trp Pro Val His Ala Val Ile Thr
                290                295                300
Asn Ser Thr Tyr Asp Gly Leu Leu Tyr Asn Thr Asp Phe Ile Lys Lys
305                     310                315                320
Thr Leu Asp Val Lys Ser Ile His Phe Asp Ser Ala Trp Val Pro Tyr
                325                330                335
Thr Asn Phe Ser Pro Ile Tyr Glu Gly Lys Cys Gly Met Ser Gly Gly
                340                345                350
Arg Val Glu Gly Lys Val Ile Tyr Glu Thr Gln Ser Thr His Lys Leu
                355                360                365
Leu Ala Ala Phe Ser Gln Ala Ser Met Ile His Val Lys Gly Asp Val
                370                375                380
Asn Glu Glu Thr Phe Asn Glu Ala Tyr Met Met His Thr Thr Thr Ser
385                     390                395                400
Pro His Tyr Gly Ile Val Ala Ser Thr Glu Thr Ala Ala Ala Met Met
                405                410                415
Lys Gly Asn Ala Gly Lys Arg Leu Ile Asn Gly Ser Ile Glu Arg Ala
                420                425                430
```

```
Ile Lys Phe Arg Lys Glu Ile Lys Arg Leu Arg Thr Glu Ser Asp Gly
        435                 440                 445

Trp Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 21
<211> LENGTH: 2148
<212> TYPE: DNA
<213> ORGANISM: Escherichia coli

<400> SEQUENCE: 21
atgaacgtta ttgcaatatt gaatcacatg ggggtttatt ttaaagaaga acccatccgt    60
gaacttcatc gcgcgcttga acgtctgaac ttccagattg tttacccgaa cgaccgtgac   120 gactattaa aactgatcga aaacaatgcg cgtctgtgcg gcgttatttt tgactgggat   180
aaatataatc tcgagctgtg cgaagaaatt agcaaaatga acgagaacct gccgttgtac   240
gcgttcgcta atacgtattc cactctcgat gtaagcctga atgacctgcg tttacagatt   300
agcttctttg aatatgcgct gggtgctgct gaagatattg ctaataagat caagcagacc   360
actgacgaat atatcaacac tattctgcct ccgctgacta aagcactgtt taaatatgtt   420
cgtgaaggta aatatacttt ctgtactcct ggtcacatgg gcggtactgc attccagaaa   480
```

```
agcccggtag gtagcctgtt ctatgatttc tttggtccga ataccatgaa atctgatatt    540
tccatttcag tatctgaact gggttctctg ctggatcaca gtggtccaca caaagaagca    600
gaacagtata tcgctcgcgt ctttaacgca gaccgcagct acatggtgac caacggtact    660
tccactgcga acaaaattgt tggtatgtac tctgctccag caggcagcac cattctgatt    720
gaccgtaact gccacaaatc gctgacccac ctgatgatga tgagcgatgt tacgccaatc    780
tatttccgcc cgacccgtaa cgcttacggt attcttggtg gtatcccaca gagtgaattc    840
cagcacgcta ccattgctaa gcgcgtgaaa gaaacaccaa cgcaacctg gccggtacat    900 gctgtaatta ccaactctac ctatgatggt ctgctgtaca caccgactt catcaagaaa    960 acactggatg tgaaatccat ccactttgac tccgcgtggg tgccttacac caacttctca   1020
ccgatttacg aaggtaaatg cggtatgagc ggtggccgtg tagaagggaa agtgatttac   1080
gaaacccagt ccactcacaa actgctggcg gcgttctctc aggcttccat gatccacgtt   1140
aaaggtgacg taaacgaaga aacctttaac gaagcctaca tgatgcacac caccacttct   1200
ccgcactacg gtatcgtggc gtccactgaa accgctgcgg cgatgatgaa aggcaatgca   1260
ggtaagcgtc tgatcaacgg ttctattgaa cgtgcgatca aattccgtaa agagatcaaa   1320
cgtctgagaa cggaatctga tggctggttc tttgatgtat ggcagccgga tcatatcgat   1380
acgactgaat gctggccgct gcgttctgac agcacctggc acggcttcaa aacatcgat   1440 aacgagcaca tgtatcttga cccgatcaaa gtcaccctgc tgactccggg gatggaaaaa   1500
gacggcacca tgagcgactt tggtattccg gccagcatcg tggcgaaata cctcgacgaa   1560
catggcatcg ttgttgagaa accggtccg tataacctgc tgttcctgtt cagcatcggt   1620
atcgataaga ccaaagcact gagcctgctg cgtgctctga ctgactttaa cgtgcgttc   1680 gacctgaacc tgcgtgtgaa aaacatgctg ccgtctctgt atcgtgaaga tcctgaattc   1740
tatgaaaaca tgcgtattca ggaactggct cagaatatcc acaaactgat tgttcaccac   1800
aatctgccgg atctgatgta tcgcgcattt gaagtgctgc cgacgatggt aatgactccg   1860
tatgctgcat tccagaaaga gctgcacggt atgaccgaag aagtttacct cgacgaaatg   1920
gtaggtcgta ttaacgccaa tatgatcctt ccgtacccgc cgggagttcc tctggtaatg   1980
ccgggtgaaa tgatcaccga gaaagccgt ccggttctgg agttcctgca gatgctgtgt   2040
gaaatcggcg ctcactatcc gggctttgaa accgatattc acggtgcata ccgtcaggct   2100
gatggccgct ataccgttaa ggtattgaaa gaagaaagca aaaaataa               2148
```

<210> SEQ ID NO 22
<211> LENGTH: 715
<212> TYPE: PRT
<213> ORGANISM: Artificial Sequence
<220> FEATURE:
<223> OTHER INFORMATION: CadA mutant K320L polypeptide sequence-
      mutation underlined

<400> SEQUENCE: 22

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
                20                  25                  30

Ile Val Tyr Pro Asn Asp Arg Asp Leu Leu Lys Leu Ile Glu Asn
            35                  40                  45

Asn Ala Arg Leu Cys Gly Val Ile Phe Asp Trp Asp Lys Tyr Asn Leu
    50                  55                  60

```
Glu Leu Cys Glu Glu Ile Ser Lys Met Asn Glu Asn Leu Pro Leu Tyr
 65                  70                  75                  80

Ala Phe Ala Asn Thr Tyr Ser Thr Leu Asp Val Ser Leu Asn Asp Leu
                 85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Leu
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
```

|  | 485 | 490 | 495 |
|---|---|---|---|

Gly Met Glu Lys Asp Gly Thr Met Ser Asp Phe Gly Ile Pro Ala Ser
500                     505                     510

Ile Val Ala Lys Tyr Leu Asp Glu His Gly Ile Val Val Glu Lys Thr
        515                     520                     525

Gly Pro Tyr Asn Leu Leu Phe Leu Phe Ser Ile Gly Ile Asp Lys Thr
        530                     535                     540

Lys Ala Leu Ser Leu Leu Arg Ala Leu Thr Asp Phe Lys Arg Ala Phe
545                     550                     555                     560

Asp Leu Asn Leu Arg Val Lys Asn Met Leu Pro Ser Leu Tyr Arg Glu
                565                     570                     575

Asp Pro Glu Phe Tyr Glu Asn Met Arg Ile Gln Glu Leu Ala Gln Asn
                580                     585                     590

Ile His Lys Leu Ile Val His His Asn Leu Pro Asp Leu Met Tyr Arg
        595                     600                     605

Ala Phe Glu Val Leu Pro Thr Met Val Met Thr Pro Tyr Ala Ala Phe
        610                     615                     620

Gln Lys Glu Leu His Gly Met Thr Glu Glu Val Tyr Leu Asp Glu Met
625                     630                     635                     640

Val Gly Arg Ile Asn Ala Asn Met Ile Leu Pro Tyr Pro Pro Gly Val
                645                     650                     655

Pro Leu Val Met Pro Gly Glu Met Ile Thr Glu Glu Ser Arg Pro Val
                660                     665                     670

Leu Glu Phe Leu Gln Met Leu Cys Glu Ile Gly Ala His Tyr Pro Gly
        675                     680                     685

Phe Glu Thr Asp Ile His Gly Ala Tyr Arg Gln Ala Asp Gly Arg Tyr
        690                     695                     700

Thr Val Lys Val Leu Lys Glu Glu Ser Lys Lys
705                     710                     715

<210> SEQ ID NO 23
<211> LENGTH: 2148
<212> TYPE: DNA
<213> ORGANISM: Artificial Sequence
<220> FEATURE:
<223> OTHER INFORMATION: Escherichia coli cadA mutant K320L nucleic acid
      sequence- mutation underlined

<400> SEQUENCE: 23

| | |
|---|---|
| atgaacgtta ttgcaatatt gaatcacatg ggggtttatt ttaaagaaga acccatccgt | 60 |
| gaacttcatc gcgcgcttga acgtctgaac ttccagattg tttacccgaa cgaccgtgac | 120 |
| gacttattaa aactgatcga aaacaatgcg cgtctgtgcg gcgttatttt tgactgggat | 180 |
| aaatataatc tcgagctgtg cgaagaaatt agcaaaatga cgagaaacct gccgttgtac | 240 |
| gcgttcgcta atacgtattc cactctcgat gtaagcctga atgacctgcg tttacagatt | 300 |
| agcttctttg aatatgcgct gggtgctgct gaagatattg ctaataagat caagcagacc | 360 |
| actgacgaat atatcaacac tattctgcct ccgctgacta agcactgtt taaatatgtt | 420 |
| cgtgaaggta atatactttt ctgtactcct ggtcacatgg gcggtactgc attccagaaa | 480 |
| agcccggtag gtagcctgtt ctatgatttc tttggtccga ataccatgaa atctgatatt | 540 |
| tccatttcag tatctgaact gggttctctg ctggatcaca gtggtccaca caaagaagca | 600 |
| gaacagtata tcgctcgcgt ctttaacgca gaccgcagct acatggtgac caacggtact | 660 |
| tccactgcga acaaaattgt tggtatgtac tctgctccag caggcagcac cattctgatt | 720 |

-continued

```
gaccgtaact gccacaaatc gctgacccac ctgatgatga tgagcgatgt tacgccaatc      780
tatttccgcc cgaccgtaa cgcttacggt attcttggtg gtatcccaca gagtgaattc      840
cagcacgcta ccattgctaa gcgcgtgaaa gaaacaccaa acgcaacctg gccggtacat      900
gctgtaatta ccaactctac ctatgatggt ctgctgtaca acaccgactt catcaagctg      960
acactggatg tgaaatccat ccactttgac tccgcgtggg tgccttacac caacttctca     1020
ccgatttacg aaggtaaatg cggtatgagc ggtggccgtg tagaagggaa agtgatttac     1080
gaaacccagt ccactcacaa actgctggcg gcgttctctc aggcttccat gatccacgtt     1140
aaaggtgacg taaacgaaga aacctttaac gaagcctaca tgatgcacac caccacttct     1200
ccgcactacg gtatcgtggc gtccactgaa accgctgcgg cgatgatgaa aggcaatgca     1260
ggtaagcgtc tgatcaacgg ttctattgaa cgtgcgatca aattccgtaa agagatcaaa     1320
cgtctgagaa cggaatctga tggctggttc tttgatgtat ggcagccgga tcatatcgat     1380
acgactgaat gctggccgct gcgttctgac agcaccctgg cacggcttcaa aaacatcgat     1440
aacgagcaca tgtatcttga cccgatcaaa gtcaccctgc tgactccggg gatggaaaaa     1500
gacggcacca tgagcgactt tggtattccg gccagcatcg tggcgaaata cctcgacgaa     1560
catggcatcg ttgttgagaa aaccggtccg tataacctgc tgttcctgtt cagcatcggt     1620
atcgataaga ccaaagcact gagcctgctg cgtgctctga ctgactttaa acgtgcgttc     1680
gacctgaacc tgcgtgtgaa aaacatgctg ccgtctctgt atcgtgaaga tcctgaattc     1740
tatgaaaaca tgcgtattca ggaactggct cagaatatcc acaaactgat tgttcaccac     1800
aatctgccgg atctgatgta tcgcgcattt gaagtgctgc cgacgatggt aatgactccg     1860
tatgctgcat tccagaaaga gctgcacggt atgaccgaag aagtttaccct cgacgaaatg     1920
gtaggtcgta ttaacgccaa tatgatcctt ccgtacccgc cgggagttcc tctggtaatg     1980
ccgggtgaaa tgatcaccga agaaagccgt ccggttctgg agttcctgca gatgctgtgt     2040
gaaatcggcg ctcactatcc gggctttgaa accgatattc acggtgcata ccgtcaggct     2100
gatggccgct ataccgttaa ggtattgaaa gaagaaagca aaaaataa                  2148
```

<210> SEQ ID NO 24
<211> LENGTH: 346
<212> TYPE: PRT
<213> ORGANISM: Artificial Sequence
<220> FEATURE:
<223> OTHER INFORMATION: Escherichia coli OmpA polypeptide sequence -
      the region used for surface display is underlined

<400> SEQUENCE: 24

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Thr Gly Ala
                20                  25                  30

Lys Leu Gly Trp Ser Gln Tyr His Asp Thr Gly Phe Ile Asn Asn Asn
            35                  40                  45

Gly Pro Thr His Glu Asn Gln Leu Gly Ala Gly Ala Phe Gly Gly Tyr
        50                  55                  60

Gln Val Asn Pro Tyr Val Gly Phe Glu Met Gly Tyr Asp Trp Leu Gly
65                  70                  75                  80

Arg Met Pro Tyr Lys Gly Ser Val Glu Asn Gly Ala Tyr Lys Ala Gln
                85                  90                  95

Gly Val Gln Leu Thr Ala Lys Leu Gly Tyr Pro Ile Thr Asp Asp Leu
            100                 105                 110

Asp Ile Tyr Thr Arg Leu Gly Gly Met Val Trp Arg Ala Asp Thr Lys
            115                 120                 125

Ser Asn Val Tyr Gly Lys Asn His Asp Thr Gly Val Ser Pro Val Phe
        130                 135                 140

Ala Gly Gly Val Glu Tyr Ala Ile Thr Pro Glu Ile Ala Thr Arg Leu
145                 150                 155                 160

Glu Tyr Gln Trp Thr Asn Asn Ile Gly Asp Ala His Thr Ile Gly Thr
                165                 170                 175

Arg Pro Asp Asn Gly Met Leu Ser Leu Gly Val Ser Tyr Arg Phe Gly
            180                 185                 190

Gln Gly Glu Ala Ala Pro Val Ala Pro Ala Pro Ala Pro Ala Pro
        195                 200                 205

Glu Val Gln Thr Lys His Phe Thr Leu Lys Ser Asp Val Leu Phe Asn
        210                 215                 220

Phe Asn Lys Ala Thr Leu Lys Pro Glu Gly Gln Ala Ala Leu Asp Gln
225                 230                 235                 240

Leu Tyr Ser Gln Leu Ser Asn Leu Asp Pro Lys Asp Gly Ser Val Val
                245                 250                 255

Val Leu Gly Tyr Thr Asp Arg Ile Gly Ser Asp Ala Tyr Asn Gln Gly
            260                 265                 270

Leu Ser Glu Arg Arg Ala Gln Ser Val Val Asp Tyr Leu Ile Ser Lys
        275                 280                 285

Gly Ile Pro Ala Asp Lys Ile Ser Ala Arg Gly Met Gly Glu Ser Asn
290                 295                 300

Pro Val Thr Gly Asn Thr Cys Asp Asn Val Lys Gln Arg Ala Ala Leu
305                 310                 315                 320

Ile Asp Cys Leu Ala Pro Asp Arg Arg Val Glu Ile Glu Val Lys Gly
                325                 330                 335

Ile Lys Asp Val Val Thr Gln Pro Gln Ala
            340                 345

<210> SEQ ID NO 25
<211> LENGTH: 211
<212> TYPE: PRT
<213> ORGANISM: Artificial Sequence
<220> FEATURE:
<223> OTHER INFORMATION: Fusion Polypeptide AA Seq containing CBH1 CBD
      fused to surface display regioni of OmpA encoded by a
      polynucleotide encoding fusion protein comprising: E. Coli
      lipoprotein leader seq, to OmpA diplay region, to CBH1 CBD

<400> SEQUENCE: 25

Met Lys Ala Thr Lys Leu Val Leu Gly Ala Val Ile Leu Gly Ser Thr
1               5                   10                  15

Leu Leu Ala Gly Cys Ser Ser Asn Ala Lys Ile Asp Gln Asn Asn Asn
            20                  25                  30

Gly Pro Thr His Glu Asn Gln Leu Gly Ala Gly Ala Phe Gly Gly Tyr
        35                  40                  45

Gln Val Asn Pro Tyr Val Gly Phe Glu Met Gly Tyr Asp Trp Leu Gly
    50                  55                  60

Arg Met Pro Tyr Lys Gly Ser Val Glu Asn Gly Ala Tyr Lys Ala Gln
65                  70                  75                  80

Gly Val Gln Leu Thr Ala Lys Leu Gly Tyr Pro Ile Thr Asp Asp Leu
                85                  90                  95

Asp Ile Tyr Thr Arg Leu Gly Gly Met Val Trp Arg Ala Asp Thr Lys
            100                 105                 110

```
Ser Asn Val Tyr Gly Lys Asn His Asp Thr Gly Val Ser Pro Val Phe
        115                 120                 125

Ala Gly Gly Val Glu Tyr Ala Ile Thr Pro Glu Ile Ala Thr Arg Ser
    130                 135                 140

Arg Val Asp Ser Gly Gly Asn Pro Pro Gly Asn Arg Gly Thr Thr
145                 150                 155                 160

Thr Thr Arg Arg Pro Ala Thr Thr Thr Gly Ser Ser Pro Gly Pro Thr
                165                 170                 175

Gln Ser His Tyr Gly Gln Cys Gly Gly Ile Gly Tyr Ser Gly Pro Thr
            180                 185                 190

Val Cys Ala Ser Gly Thr Thr Cys Gln Val Leu Asn Pro Tyr Tyr Ser
        195                 200                 205

Gln Cys Leu
    210

<210> SEQ ID NO 26
<211> LENGTH: 52
<212> TYPE: DNA
<213> ORGANISM: Artificial Sequence
<220> FEATURE:
<223> OTHER INFORMATION: Primer cadA-F1

<400> SEQUENCE: 26
ggcgagctca cacaggaaac agaccatgaa cgttattgca atattgaatc ac       52

<210> SEQ ID NO 27
<211> LENGTH: 28
<212> TYPE: DNA
<213> ORGANISM: Artificial Sequence
<220> FEATURE:
<223> OTHER INFORMATION: Primer cadA-R1

<400> SEQUENCE: 27
ggctctagac cacttccctt gtacgagc                                   28

<210> SEQ ID NO 28
<211> LENGTH: 29
<212> TYPE: DNA
<213> ORGANISM: Artificial Sequence
<220> FEATURE:
<223> OTHER INFORMATION: Primer npt-F1

<400> SEQUENCE: 28
ggcaagctta agagacagga tgaggatcg                                  29

<210> SEQ ID NO 29
<211> LENGTH: 30
<212> TYPE: DNA
<213> ORGANISM: Artificial Sequence
<220> FEATURE:
<223> OTHER INFORMATION: Primer npt-R1

<400> SEQUENCE: 29
ggccatatgt cagaagaact cgtcaagaag                                 30

<210> SEQ ID NO 30
<211> LENGTH: 47
<212> TYPE: DNA
<213> ORGANISM: Artificial Sequence
<220> FEATURE:
<223> OTHER INFORMATION: Primer cadA-F2

<400> SEQUENCE: 30
```
atttcacaca ggaaacagct atgaacgtta ttgcaatatt gaatcac        47

<210> SEQ ID NO 31
<211> LENGTH: 20
<212> TYPE: DNA
<213> ORGANISM: Artificial Sequence
<220> FEATURE:
<223> OTHER INFORMATION: Primer cadA-R2

<400> SEQUENCE: 31
agctgtttcc tgtgtgaaat        20

<210> SEQ ID NO 32
<211> LENGTH: 33
<212> TYPE: DNA
<213> ORGANISM: Artificial Sequence
<220> FEATURE:
<223> OTHER INFORMATION: Primer lpp-F1

<400> SEQUENCE: 32
ggcgagctca tgaaagctac taaactggta ctg        33

<210> SEQ ID NO 33
<211> LENGTH: 20
<212> TYPE: DNA
<213> ORGANISM: Artificial Sequence
<220> FEATURE:
<223> OTHER INFORMATION: Primer lpp-R1

<400> SEQUENCE: 33
ctgatcgatt ttagcgttgc        20

<210> SEQ ID NO 34
<211> LENGTH: 38
<212> TYPE: DNA
<213> ORGANISM: Artificial Sequence
<220> FEATURE:
<223> OTHER INFORMATION: Primer lpp-ompA-F

<400> SEQUENCE: 34
gcaacgctaa aatcgatcag aacaacaatg gcccgacc        38

<210> SEQ ID NO 35
<211> LENGTH: 29
<212> TYPE: DNA
<213> ORGANISM: Artificial Sequence
<220> FEATURE:
<223> OTHER INFORMATION: Primer ompA-R

<400> SEQUENCE: 35
ggctctagaa cgggtagcga tttcaggag        29

<210> SEQ ID NO 36
<211> LENGTH: 44
<212> TYPE: DNA
<213> ORGANISM: Artificial Sequence
<220> FEATURE:
<223> OTHER INFORMATION: Primer lpp-F2

<400> SEQUENCE: 36
atttcacaca ggaaacagct atgaaagcta ctaaactggt actg        44

<210> SEQ ID NO 37
<211> LENGTH: 20
<212> TYPE: DNA

<213> ORGANISM: Artificial Sequence
<220> FEATURE:
<223> OTHER INFORMATION: Primer lpp-R2

<400> SEQUENCE: 37
agctgtttcc tgtgtgaaat                                              20

<210> SEQ ID NO 38
<211> LENGTH: 35
<212> TYPE: DNA
<213> ORGANISM: Artificial Sequence
<220> FEATURE:
<223> OTHER INFORMATION: Primer XynA-F

<400> SEQUENCE: 38
ggctctagag tcgacgcgac ctgctcttac aacat                             35

<210> SEQ ID NO 39
<211> LENGTH: 38
<212> TYPE: DNA
<213> ORGANISM: Artificial Sequence
<220> FEATURE:
<223> OTHER INFORMATION: Primer XynA-R

<400> SEQUENCE: 39
ggcgcatgcc tgcagttact gctgattacc agagctgc                          38

<210> SEQ ID NO 40
<211> LENGTH: 35
<212> TYPE: DNA
<213> ORGANISM: Artificial Sequence
<220> FEATURE:
<223> OTHER INFORMATION: Primer CBH1-F

<400> SEQUENCE: 40
ggctctagag tcgactctgg tggtaacccg ccagg                             35

<210> SEQ ID NO 41
<211> LENGTH: 38
<212> TYPE: DNA
<213> ORGANISM: Artificial Sequence
<220> FEATURE:
<223> OTHER INFORMATION: Primer CBH1-R

<400> SEQUENCE: 41
ggcgcatgcc tgcagttaca ggcactgaga gtagtacg                          38

<210> SEQ ID NO 42
<211> LENGTH: 35
<212> TYPE: DNA
<213> ORGANISM: Artificial Sequence
<220> FEATURE:
<223> OTHER INFORMATION: Primer CBH2-F

<400> SEQUENCE: 42
ggctctagag tcgacgtttg gggtcagtgc ggtgg                             35

<210> SEQ ID NO 43
<211> LENGTH: 38
<212> TYPE: DNA
<213> ORGANISM: Artificial Sequence
<220> FEATURE:
<223> OTHER INFORMATION: Primer CBH2-R

<400> SEQUENCE: 43
ggcgcatgcc tgcagttaac caaccggcgg aacacgag                          38

<210> SEQ ID NO 44
<211> LENGTH: 35
<212> TYPE: DNA
<213> ORGANISM: Artificial Sequence
<220> FEATURE:
<223> OTHER INFORMATION: Primer CEX-F

<400> SEQUENCE: 44
ggctctagag tcgacggtgc gtctcctacc ccaac                    35

<210> SEQ ID NO 45
<211> LENGTH: 38
<212> TYPE: DNA
<213> ORGANISM: Artificial Sequence
<220> FEATURE:
<223> OTHER INFORMATION: Primer CEX-R

<400> SEQUENCE: 45
ggcgcatgcc tgcagttaac caacggtgca cggggtac                 38

<210> SEQ ID NO 46
<211> LENGTH: 33
<212> TYPE: DNA
<213> ORGANISM: Artificial Sequence
<220> FEATURE:
<223> OTHER INFORMATION: Primer CCBP-F

<400> SEQUENCE: 46
ggctctagag tcgacaccac tccaacccca acg                      33

<210> SEQ ID NO 47
<211> LENGTH: 38
<212> TYPE: DNA
<213> ORGANISM: Artificial Sequence
<220> FEATURE:
<223> OTHER INFORMATION: Primer CCBP-R

<400> SEQUENCE: 47
ggcgcatgcc tgcagttacg ttacggcaga cgcggtcg                 38

<210> SEQ ID NO 48
<211> LENGTH: 29
<212> TYPE: DNA
<213> ORGANISM: Artificial Sequence
<220> FEATURE:
<223> OTHER INFORMATION: Primer cadA-F3

<400> SEQUENCE: 48
ggctctagaa tttcacacag gaaacagct                           29

<210> SEQ ID NO 49
<211> LENGTH: 20
<212> TYPE: DNA
<213> ORGANISM: Artificial Sequence
<220> FEATURE:
<223> OTHER INFORMATION: Primer npt-F2

<400> SEQUENCE: 49
caaggcgcgt atgcccgacg                                     20

<210> SEQ ID NO 50
<211> LENGTH: 20
<212> TYPE: DNA
<213> ORGANISM: Artificial Sequence
<220> FEATURE:

```
<223> OTHER INFORMATION: Primer npt-R2

<400> SEQUENCE: 50
cgtcgggcat acgcgccttg                                                    20

<210> SEQ ID NO 51
<211> LENGTH: 39
<212> TYPE: DNA
<213> ORGANISM: Artificial Sequence
<220> FEATURE:
<223> OTHER INFORMATION: Primer K320L-F

<400> SEQUENCE: 51
accgacttca tcaagctgac actggatgtg aaatccatc                                39

<210> SEQ ID NO 52
<211> LENGTH: 39
<212> TYPE: DNA
<213> ORGANISM: Artificial Sequence
<220> FEATURE:
<223> OTHER INFORMATION: Primer K320L-R

<400> SEQUENCE: 52
gatttcacat ccagtgtcag cttgatgaag tcggtgttg                                39
```